(12) United States Patent
Tillekeratne et al.

(10) Patent No.: US 11,098,038 B2
(45) Date of Patent: Aug. 24, 2021

(54) IMIDAZOLE-BASED ANTICANCER AGENTS AND DERIVATIVES THEREOF, AND METHODS OF MAKING AND USING SAME

(71) Applicant: The University of Toledo, Toledo, OH (US)

(72) Inventors: Viranga Tillekeratne, Toledo, OH (US); Ayad Al-Hamashi, Toledo, OH (US); Samkeliso Dlamini, Toledo, OH (US); Abdulateef Saeed S. Alqahtani, Toledo, OH (US); Endri Karaj, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/638,587

(22) PCT Filed: Aug. 17, 2018

(86) PCT No.: PCT/US2018/046897
§ 371 (c)(1),
(2) Date: Feb. 12, 2020

(87) PCT Pub. No.: WO2019/036607
PCT Pub. Date: Feb. 21, 2019

(65) Prior Publication Data
US 2020/0385374 A1    Dec. 10, 2020

Related U.S. Application Data

(60) Provisional application No. 62/546,829, filed on Aug. 17, 2017.

(51) Int. Cl.
*C07D 417/12* (2006.01)
*C07D 233/64* (2006.01)

(52) U.S. Cl.
CPC ......... *C07D 417/12* (2013.01); *C07D 233/64* (2013.01)

(58) Field of Classification Search
CPC ........................... C07D 417/12; C07D 233/64
See application file for complete search history.

(56) References Cited

U.S. PATENT DOCUMENTS

| 7,135,493 B2 | 11/2006 | Urano et al. |
| 7,345,174 B2 | 3/2008 | Breslow et al. |
| 7,943,650 B2 | 5/2011 | Gupta et al. |
| 2014/0163009 A1 | 6/2014 | Luckhurst et al. |

FOREIGN PATENT DOCUMENTS

WO    2011146855 A1    11/2011

OTHER PUBLICATIONS

Cancer and Metastasis Reviews (1998), 17(1), 91-106.*
Science (1999), vol. 286, 531-537.*
PCT Search Report and Written Opinion, Application No. PCT/US18/46897, dated Nov. 1, 2018.

* cited by examiner

*Primary Examiner* — Rebecca L Anderson
(74) *Attorney, Agent, or Firm* — MacMillan, Sobanski & Todd, LLC

(57) ABSTRACT

Imidazole-based anticancer agents and derivatives thereof, as well as methods of making and methods of using the same, are described. The imidazole-based anticancer agents are HDAC inhibitor compounds having a 1-(1H-imidazol-2-yl)ethan-1-one or 1-(1H-imidazol-2-yl)ethane-1-thione moiety.

35 Claims, 10 Drawing Sheets
(5 of 10 Drawing Sheet(s) Filed in Color)

FIG. 4C

IMIDAZOLE-BASED ANTICANCER AGENTS AND DERIVATIVES THEREOF, AND METHODS OF MAKING AND USING SAME

RELATED APPLICATIONS

This application is a national stage application filed under 35 U.S.C. § 371 of international application PCT/US18/046897, filed under the authority of the Patent Cooperation Treaty on Aug. 17, 2018, which claims priority to U.S. Provisional Application No. 62/546,829 filed under 35 U.S.C. § 111(b) on Aug. 17, 2017, the disclosure of which is incorporated herein by reference in its entirety for all purposes.

STATEMENT REGARDING FEDERALLY SPONSORED RESEARCH

This invention was made with no government support. The government has no rights in this invention.

BACKGROUND OF THE INVENTION

Cancer is the second leading cause of death in the United States. Despite advances in the treatment strategies, significant limitations still remain. Selectively treating cancer cells without affecting normal cells is a challenging task. There are many types of anticancer drugs in clinical use, but they all have limitations. There is a need for new and improved anticancer drugs which act by different mechanisms, especially to overcome multiple drug resistance.

Histone deacetylases (HDACs) are highly expressed in cancer cells, and inhibition of HDAC enzymes is a strategy for cancer drug development. HDAC inhibitors have multiple modes of inhibiting their target, thus making them candidates for cancer treatment with low drug resistance. HDACs have the ability to influence crucial cellular processes through control of crucial modulators which play a key role in genetic transcription to gene expression, cellular growth, and survival. Through these effects, HDACs have a direct role in the mitotic process of a cell. This occurs through enzymatic cleavage of the acetyl groups located on histone lysine residues, which in turn modifies gene transcription, expression, cell growth, and survival. Furthermore, HDACs control the acetylation of non-histone proteins responsible for tumor suppression such as p53. There is a connection between cancer and surge in HDAC expression in the cell. Over expression of HDACs has been linked with the onset of cancers and therefore, HDACs are considered targets for drug intervention.

HDAC proteins are involved in the regulation of acetylation status of non-histone proteins as well. Therefore, such enzymes play an important role in regulating many cellular functions, in addition to transcription. This means that the application of HDAC inhibitors can be expanded to other disease states such as inflammatory diseases, autoimmune disease, and diseases caused by microbes and viruses. For example, HDAC inhibitors have applications in the treatment or management of myocardial infarction, malaria, leukemia, and HIV, among others.

Some HDAC inhibitors have been developed as anticancer agents. Unfortunately, currently available HDAC inhibitors are not selective and have undesirable side effects. Selective inhibition of specific HDAC isoforms to preferentially suppress the proliferation of cancer cells is a goal yet to be achieved. Therefore, new and improved HDAC inhibitors, particularly HDAC inhibitors that are more selective, are needed to mitigate side effects and improve potency.

SUMMARY OF THE INVENTION

Provided is a compound comprising Formula I:

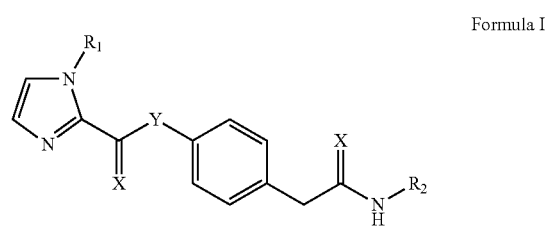

Formula I where each X is independently O or S; Y is C—C, C=C, or a cyclopropyl ring; $R_1$ is hydrogen, alkyl, aryl, heteroaryl, aralkyl, or heteroaralkyl; and $R_2$ is hydrogen, alkyl, aryl, heteroaryl, aralkyl, or heteroaralkyl. Also provided are salts, stereoisomers, racemates, hydrates, solvates, prodrugs, and polymorphs of Formula I.

In certain embodiments, either of $R_1$ or $R_2$ is H, alkyl, substituted or unsubstituted phenyl, cyclohexyl, or napthalyl. In certain embodiments, either of $R_1$ or $R_2$ is selected from the group consisting of H, methyl, ethyl, phenyl, naphthalyl, 4-dimethylaminophenyl, 4-methoxyphenyl, p-tolyl, 4-fluorophenyl, cyclohexyl, 4-trifluoromethylphenyl, and 4-chlorophenyl. In certain embodiments, each of $R_1$ and $R_2$ is independently selected from the group consisting of H, methyl, ethyl, phenyl, naphthalyl, 4-dimethylaminophenyl, 4-methoxyphenyl, p-tolyl, 4-fluorophenyl, cyclohexyl, 4-trifluoromethylphenyl, and 4-chlorophenyl.

In certain embodiments, each X is O, and Y is C=C, such that the compound comprises Formula II:

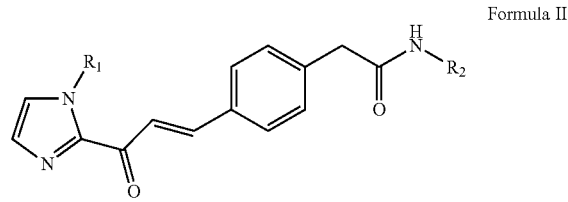

Formula II

In certain embodiments, each X is O, and $R_1$ is H, such that the compound comprises Formula III:

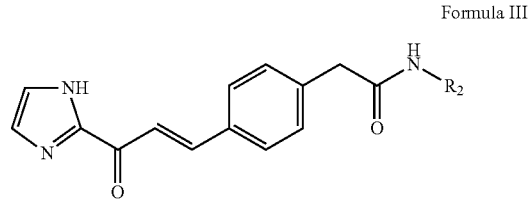

Formula III

In certain embodiments, each X is O, and Y is a cyclopropyl ring, such that the compound comprises Formula IV:

Formula IV

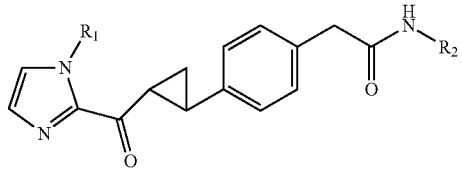

In certain embodiments, the compound comprises Formula V:

Formula V

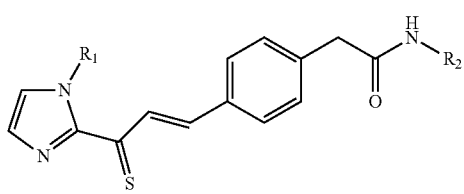

In certain embodiments, the compound comprises Formula VI:

Formula VI

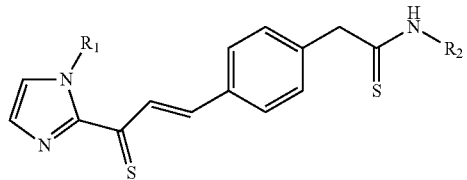

In certain embodiments, the compound comprises (E)-2-(4-(3-(1H-imidazol-2-yl)-3-oxoprop-1-en-1-yl)phenyl)-N-(naphthalen-1-yl)acetamide 17:

17

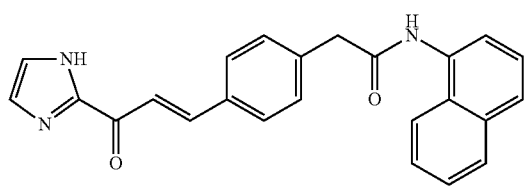

In certain embodiments, the compound comprises (E)-2-(4-(3-(1H-imidazol-2-yl)-3-oxoprop-1-en-1-yl)phenyl)-N-(4-(dimethylamino)phenyl)acetamide 18:

18

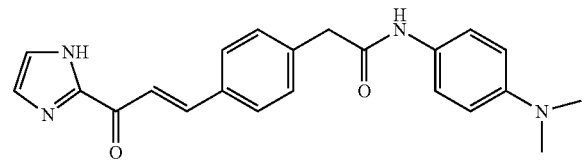

In certain embodiments, the compound comprises (E)-2-(4-(3-(1H-imidazol-2-yl)-3-oxoprop-1-en-1-yl)phenyl)-N-(4-methoxyphenyl) acetamide 19:

19

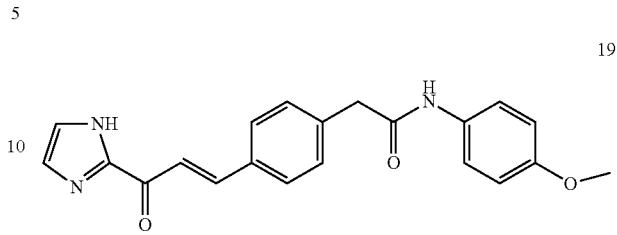

In certain embodiments, the compound comprises (E)-2-(4-(3-(1H-imidazol-2-yl)-3-oxoprop-1-en-1-yl)phenyl)-N-(p-tolyl)acetamide 20:

20

In certain embodiments, the compound comprises (E)-2-(4-(3-(1H-imidazol-2-yl)-3-oxoprop-1-en-1-yl)phenyl)-N-phenylacetamide 21:

21

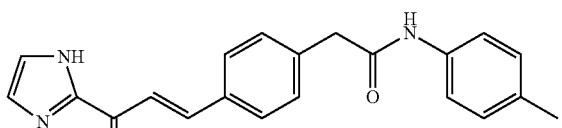

In certain embodiments, the compound comprises (E)-2-(4-(3-(1H-imidazol-2-yl)-3-oxoprop-1-en-1-yl)phenyl)-N-(4-fluorophenyl) acetamide 22:

22

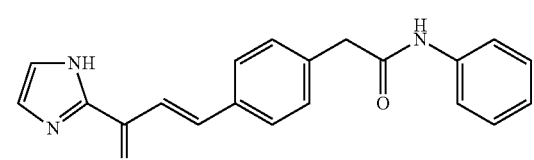

In certain embodiments, the compound comprises (E)-2-(4-(3-(1H-imidazol-2-yl)-3-oxoprop-1-en-1-yl)phenyl)-N-cyclohexyl acetamide 23:

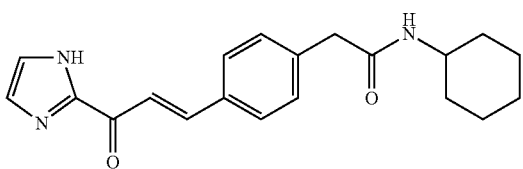

23

In certain embodiments, the compound comprises (E)-2-(4-(3-(1H-imidazole-2-yl)-3-oxoprop-1-en-1-yl)phenyl)-N-(4-(trifluoromethyl)phenyl)acetamide 24:

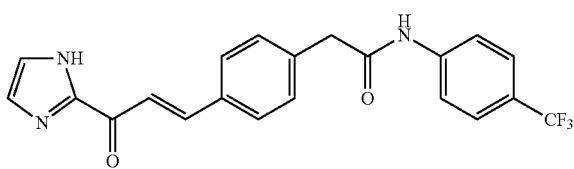

24

In certain embodiments, the compound comprises (E)-2-(-4(3-(1H-imidazol-2-yl)-3-oxoprop-1-en-1-yl)phenyl)-N-(4-chlorophenyl)acetamide 25:

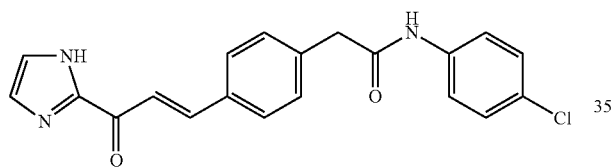

25

In certain embodiments, the compound comprises (E)-2-(4-(3-(1-methyl-1H-imidazol-2-yl)-3-oxoprop-1-en-1-yl)phenyl)-N-(4-(trifluoromethyl)phenyl)acetamide 26:

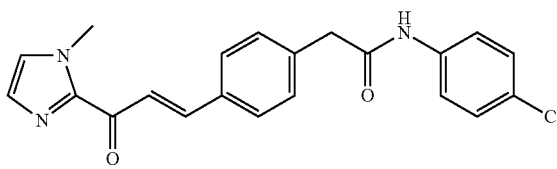

26

In certain embodiments, the compound comprises (E)-2-(4-(3-(1-methyl-1H-imidazol-2-yl)-3-oxoprop-1-en-1-yl)phenyl)-N-phenylacetamide 27:

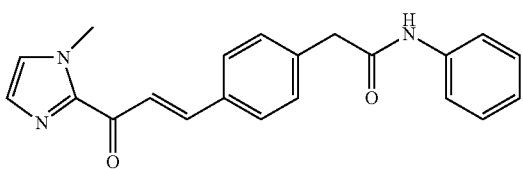

27

In certain embodiments, the compound comprises (E)-N-(4-fluorophenyl)-2-(4-(3-(1-methyl-1H-imidazol-2-yl)-3-oxoprop-1-en-1-yl)phenyl)acetamide 28:

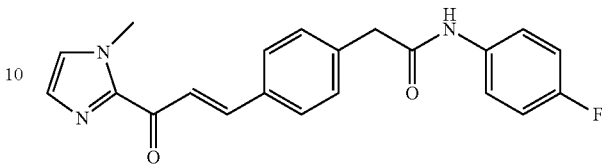

28

In certain embodiments, the compound comprises (E)-N-cyclohexyl-2-(4-(3-(1-methyl-1-H-imidazol-2-yl)-3-oxo-prop-1-en-1-yl) phenyl) acetamide 29:

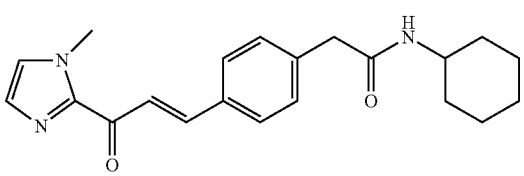

29

In certain embodiments, the compound comprises (E)-N-(4-chlorophenyl)-2-(4-(3-(1-methyl-1H-imidazol-2-yl)-3-oxoprop-1-en-1-yl) phenyl)acetamide 30:

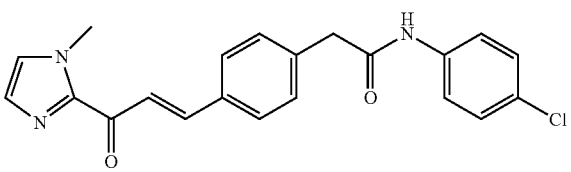

30

In certain embodiments, the compound comprises (E)-2-(4-(3-(1-ethyl-1H-imidazol-2-yl)-3-oxoprop-1-en-1-yl)phenyl)-N-(4-fluorophenyl)acetamide 31:

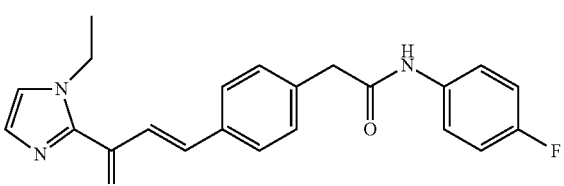

31

In certain embodiments, the compound comprises 2-(4-(3-(1H-imidazol-2-yl)-3-oxopropyl)phenyl)-N-phenylacetamide 32:

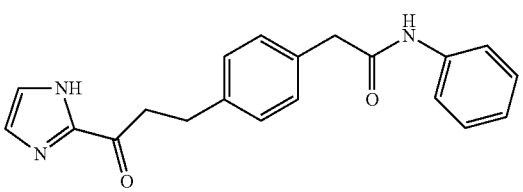

In certain embodiments, the compound comprises (E)-2-(4-(3-(1H-imidazol-2-yl)-3-oxoprop-1-en-1-yl) phenyl)-N-(3,4,5-trifluorophenyl) acetamide 33

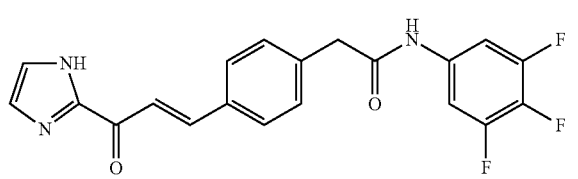

In certain embodiments, the compound comprises (E)-2-(4-(3-(1-methyl-1H-imidazol-2-yl)-3-oxoprop-1-en-1-yl) phenyl)-N-(3,4,5-trifluorophenyl)acetamide 34

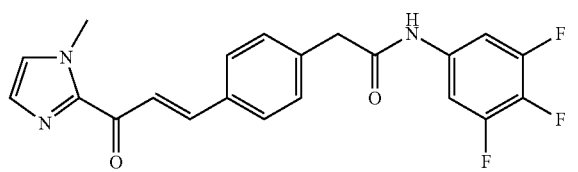

In certain embodiments, the compound comprises (E)-2-(4-(3-(1H-imidazol-2-yl)-3-oxoprop-1-en-1-yl) phenyl)-N-(perfluorophenyl)acetamide 35

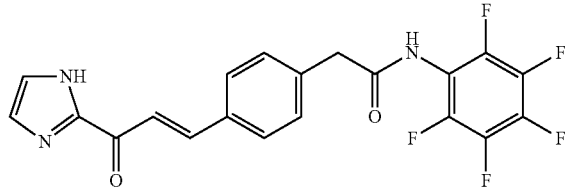

In certain embodiments, the compound comprises (E)-2-(4-(3-(1-methyl-1H-imidazol-2-yl)-3-oxoprop-1-en-1-yl) phenyl)-N-(perfluorophenyl)acetamide 36

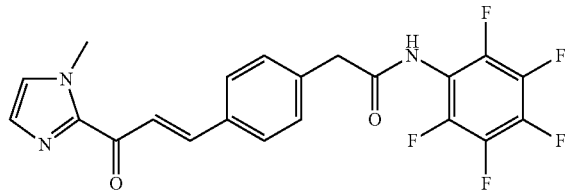

In certain embodiments, the compound comprises (E)-2-(4-(3-(1H-imidazol-2-yl)-3-oxoprop-1-en-1-yl) phenyl)-N-(3,5-bis(trifluoromethyl)phenyl) acetamide 37

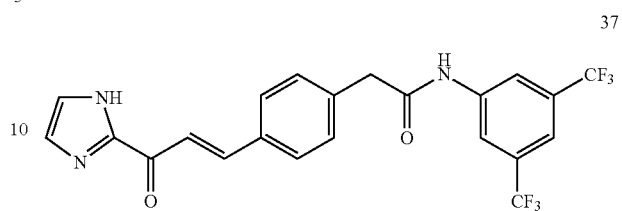

In certain embodiments, the compound comprises (E)-N-(3,5-Bis(trifluoromethyl)phenyl)-2-(4-(3-(1-methyl-1H-imidazol-2-yl)-3-oxoprop-1-en-1-yl) phenyl) acetamide 38

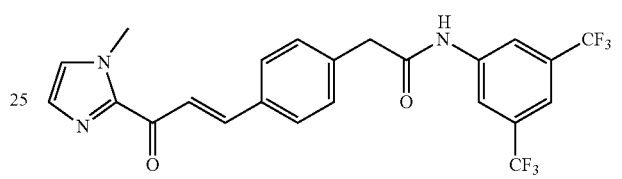

In certain embodiments, the compound comprises (E)-2-(4-(3-(1-methyl-1H-imidazol-2-yl)-3-oxoprop-1-en-1-yl) phenyl)-N-(4-(5-methylbenzo[d]thiazol-2-yl)phenyl)acetamide 39

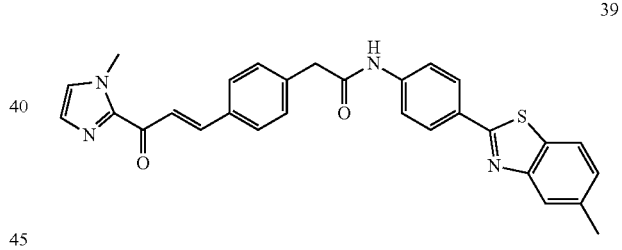

In certain embodiments, the compound comprises (E)-N-(3-azido-5-(azidomethyl)phenyl)-2-(4-(3-(1-methyl-1H-imidazol-2-yl)-3-oxoprop-1-en-1-yl)phenyl)acetamide 40

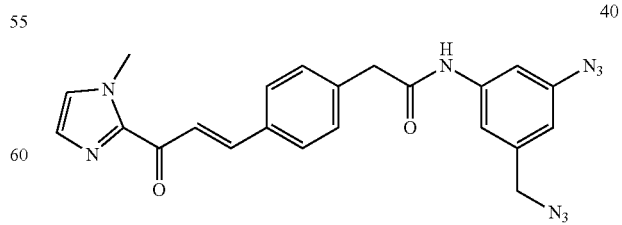

In certain embodiments, the compound comprises (E)-N-(4-ethynylphenyl)-2-(4-(3-(1-methyl-1H-imidazol-2-yl)-3-oxoprop-1-en-1-yl)phenyl) acetamide 41

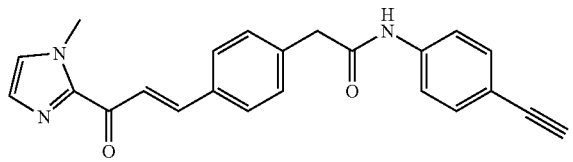

41

Further provided is a pharmaceutical composition comprising a compound of Formula I, and a pharmaceutically acceptable carrier, diluent, or adjuvant.

Further provided is a histone deactylase (HDAC) inhibitor comprising a compound consisting of a metal binding group attached to a linker and a cap group attached to the linker, wherein the metal binding group comprises 1-(1H-imidazol-2-yl)ethan-1-one or 1-(1H-imidazol-2-yl)ethane-1-thione, the linker comprises an aromatic or saturated or unsaturated aliphatic group, and the cap group comprises an aromatic, heteroaromatic, or aliphatic group.

Further provided is a method of making an HDAC inhibitor compound, the method comprising producing an aldehyde by either: (a) Heck coupling a bromoester with a styrene to produce a coupled styrene, and subjecting the coupled styrene to hydrolysis, amide formation, and oxidative cleaving of an olefinic double bond to produce an aldehyde; or (b) carbonylating a bromoester to form a carbonylated bromoester, and subjecting the carbonylated bromoester to ester hydrolysis and amide formation to produce an aldehyde; reacting the aldehyde with a tosyl-protected imidazole ketone in an aldol reaction with simultaneous removal of tosyl protecting group to produce an HDAC inhibitor compound.

In certain embodiments, the tosyl-protected imidazole ketone is produced by tosylating 1-H-imidazole-2-carboxaldehyde to produce an aldehyde, and treating the aldehyde with MeMgBr followed by Dess-Martin periodinane oxidation to produce the tosyl-protected imidazole ketone. In particular embodiments, the tosyl group is removed by heating with piperidine in anhydrous methanol or in a microwave synthesizer, followed by N-alkylation using methyl iodide in the presence of potassium carbonate in anhydrous acetonitrile or DMF to give an N-methyl ketone.

Further provided is a method of making an HDAC inhibitor compound, the method comprising coupling a styrene and a bromoester via palladium-catalyzed Heck coupling to produce an alkene; saponifying the alkene to produce a saponofied alkene, and subjecting the saponified alkene to amide coupling with an amine to produce an amide; oxidatively cleaving the amide with osmium tetroxide and sodium periodate to produce an aldehyde; and reacting the aldehyde with a tosyl-protected imidazole ketone in an aldol reaction with simultaneopus removal tosyl protecting group by heating with piperidine to produce an HDAC inhibitor compound. In certain embodiments, the method further comprises subjecting the HDAC inhibitor compound to an aldol reaction or alkylation to produce an N1 alkylated analog of the HDAC inhibitor compound. In certain embodiments, the method further comprises converting the HDAC inhibitor compound to a corresponding thione by reacting the HDAC inhibitor compound with Lawesson's reagent. In certain embodiments, the method further comprises converting the HDAC inhibitor compound to a corresponding cyclopropyl derivative by cyclopropanating the HDAC inhibitor compound with carbenoid reagents, iodomethylzinc iodide, diazomethane, and trimethylsulfoxonium iodide.

Further provided is a method of inhibiting cancer cell proliferation, the method comprising administering to cancer cells an effective amount of a compound of Formula I, and inhibiting the proliferation of the cancer cells, wherein the cancer is selected from the group consisting of: leukemia, non-small cell lung cancer, colon cancer, CNS cancer, melanoma, ovarian cancer, renal cancer, prostate cancer, and breast cancer.

Further provided is a method of treating a cancer, the method comprising administering an effective amount of a compound of Formula I to a subject in need thereof, and treating a cancer in the subject. In certain embodiments, the cancer is leukemia, non-small cell lung cancer, colon cancer, CNS cancer, melanoma, ovarian cancer, renal cancer, prostate cancer, or breast cancer.

Further provided is a method of evaluating mechanisms of cell death, the method comprising administering an effective amount of a compound of Formula I to a cell to cause cell death, and determining the mechanism of the cell death.

Further provided is a method of disrupting chromosome alignment in a cell, the method comprising administering to a cell an effective amount of a compound of Formula I, and disrupting chromosome alignment in the cell. In certain embodiments, the compound comprises (E)-2-(-4(3-(1H-imidazol-2-yl)-3-oxoprop-1-en-1-yl)phenyl)-N-(4-chlorophenyl)acetamide (25).

Further provided is a method of obliterating proper spindle function in a cell, the method comprising administering to a cell an effective amount of a combination of a compound of Formula I and an Aurora kinase inhibitor, and obliterating proper spindle function in the cell. In certain embodiments, the compound comprises (E)-2-(-4(3-(1H-imidazol-2-yl)-3-oxoprop-1-en-1-yl)phenyl)-N-(4-chlorophenyl)acetamide (25). In certain embodiments, the Aurora kinase inhibitor comprises ZM447439.

Further provided is a kit for making an HDAC inhibitor compound, the kit comprising a first container housing an aldehyde; and a second container housing a tosyl-protected imidazole ketone. In certain embodiments, the kit further comprises piperidine for carrying out aldol reaction and removing a tosyl protecting group, or one or more reagents for converting an HDAC inhibitor compound to a corresponding thione, N1 alkylated analog, or cyclopropyl derivative.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 4C: Table showing the identities of $R_1$ and $R_2$ in Scheme in FIG. 4A.

DETAILED DESCRIPTION OF THE INVENTION

Figure 1:
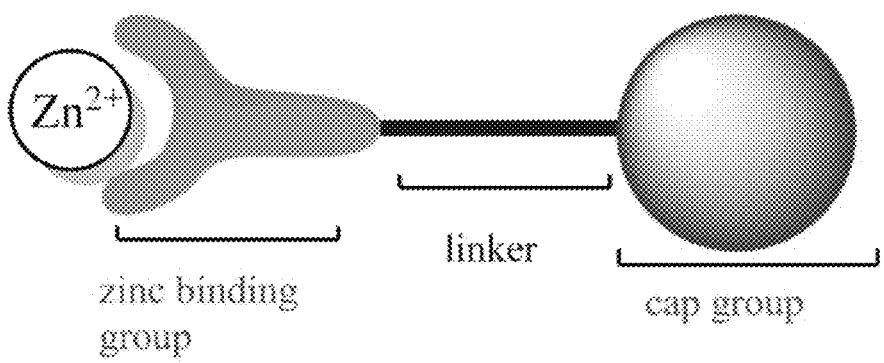
FIG. 1: Pharmacophore of HDAC inhibitors.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Definitions

For convenience, various terms used herein are defined prior to further description of the various embodiments of the present disclosure.

Unless stereochemistry is specifically indicated, all stereoisomers of the compounds herein are included, as pure compounds as well as mixtures thereof.

The term "composition" as used herein is intended to encompass a product comprising the specified ingredients in the specified amounts, as well as any product that results, directly or indirectly, from combinations of the specified ingredients in the specified amounts.

The term "protecting group" as used herein refers to a group which is introduced onto a functional group in a compound and which modifies that functional group's chemical reactivity. Typically, the protecting group modifies the functional group's chemical activity in such a way that it renders the functional group chemically inert to the reaction conditions used when a subsequent chemical transformation is effected on the compound.

The term "alkyl" refers to monovalent alkyl groups having from 1 to 50 carbon atoms, preferably having from 1 to 10 carbon atoms, and more preferably having from 1 to 6 carbon atoms. This term is exemplified by groups such as methyl, ethyl, n-propyl, iso-propyl, n-butyl, iso-butyl, n-hexyl, and the like. "Substituted alkyl" refers to an alkyl group, preferably of from 1 to 10 carbon atoms, having from 1 to 3 substituents selected from the group consisting of alkoxy, substituted alkoxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, aryloxy, thioaryloxy, heteroaryloxy, thioheteroaryloxy, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, and heterocyclic.

The term "aryl" refers to an unsaturated aromatic carbocyclic group, preferably of from 6 to 14 carbon atoms, having a single ring (e.g., phenyl) or multiple condensed rings (e.g., naphthyl or anthryl), preferably having from 1 to 3 rings. Preferred aryls include phenyl, naphthyl, and the like. Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, heterocyclic, and the like. Preferred substituents include alkyl, alkoxy, halo, cyano, nitro, trihalomethyl, and thioalkoxy.

The term "heteroaryl" refers to a group that is both heterocyclic and aromatic.

The term "aralkyl" refers to a group derived from an alkyl radical by replacing one or more hydrogen atoms with aryl groups. Thus, the term "aralkyl" refers to alkylene-aryl groups. Preferably, aralkyl groups have from 1 to 10 carbon atoms in the alkylene moiety and from 6 to 10 carbon atoms in the aryl moiety, however other aralkyl groups are entirely possible and encompassed within the present disclosure.

The term "heteroaralkyl" refers to an aralkyl group having a heterocyclic moiety.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

It will be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents or organic compounds. Combinations of substituents and variables envisioned are preferably those that result in the formation of stable compounds useful in the treatment, for example, of proliferative disorders including, but not limited to, cancer.

The term "stable" as used herein refers to compounds which possess stability sufficient to allow manufacture and which maintain the integrity of the compound for a sufficient period of time to be detected and preferably for a sufficient period of time to be useful for the purposes detailed herein.

The term "therapeutically effective amount" as used herein means that amount of active compound or pharmaceutical agent that elicits the biological or medicinal response in a tissue system, animal, or human that is being sought by a researcher, veterinarian, medical doctor, or other clinician, which includes alleviation of the symptoms of the disease or disorder being treated.

The term "pharmaceutically acceptable salt" means a salt of a compound. Suitable pharmaceutically acceptable salts of the compounds include acid addition salts which may, for example, be formed by mixing a solution of the compound with a solution of a pharmaceutically acceptable acid.

The term "pharmaceutically acceptable carrier" means a medium that is used to prepare a desired dosage form of the compound. A pharmaceutically acceptable carrier includes solvents, diluents, or other liquid vehicles; dispersion or suspension aids; surface active agents; isotonic agents; thickening or emulsifying agents; preservatives; solid binders; lubricants; and the like.

The abbreviation "HDAC" refers to histone deacetylase. The abbreviation "SAHA" refers to suberoylanilide hydroxamic acid. The abbreviation "HDACi" refers to a histone deacetylase inhibitor. The abbreviation "NMR" refers to nuclear magnetic resonance.

General Description

The basic pharmacophore of HDAC inhibitors includes a metal-binding group, a linker, and a cap group. (FIG. 1.) The metal-binding group binds to a metal ion in the metallo-enzyme's active site. Most metal-binding group are only selective towards metallo-enzymes over non-metallo enzymes, but not selective towards isoforms of the same metallo enzyme. HDAC inhibitors' metal-binding group forms ionic interactions with the $Zn^{2+}$ ion located in the active site pocket of the enzyme, inhibiting the catalysis of the substrate by the enzyme. The linker has properties similar to those of a lysine chain found on the backbone of histone. The zinc-binding group is connected to the cap group via the linker. The linker can be aromatic or aliphatic and also, saturated or unsaturated. The cap group interacts with residues on the surface of the rim at the opening to the HDAC active site. The rim has fewer conserved amino acids and therefore, the potency and the selectivity of HDAC inhibitors may be modulated by changing the nature of the cap group.

There are four HDAC inhibitor anticancer drugs approved by the US FDA currently in clinical use: vorinostat (SAHA), romidepsin (FK228), belinostat (PXD-101), and panobinostat (LBH589). The most popular zinc-binding group among these drugs is the hydroxamic acid moiety. All HDAC inhibitor drugs currently available in the market, with the exception of romidepsin, have a hydroxamate as the zinc-binding group (ZBG). These HDAC inhibitors have shown significant potency on cancer cells. However, they also exhibit many side effects, partly due to hydroxamate group's high binding affinity to metal ions. They are promiscuous and bind to different metallo-proteins, thus contributing to poor selectivity.

Provided herein is a class of HDAC inhibitors incorporating an imidazole-based metal binding group. In particular, provided herein are HDAC inhibitors having either 1-(1H-imidazol-2-yl)ethan-1-one or 1-(1H-imidazol-2-yl)ethane-1-thione as the metal binding group, a linker composed of aromatic and saturated and unsaturated aliphatic groups, and a cap group composed of aromatic, heteroaromatic, and aliphatic groups of varying size.

The HDAC inhibitor compounds provided herein have the following general Formula I:

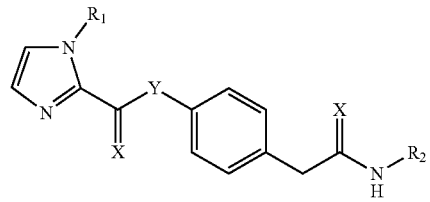

Formula I where each X is independently O or S; Y is C—C, C═C, or a cyclopropyl ring; $R_1$ is hydrogen, alkyl, aryl, heteroaryl, aralkyl, or heteroaralkyl; and $R_2$ is hydrogen, alkyl, aryl, heteroaryl, aralkyl, or heteroaralkyl. Also provided are salts, stereoisomers, racemates, hydrates, solvates, prodrugs, and polymorphs of Formula I. The compounds of Formula I have a metal-binding group distinct from known HDAC inhibitors, and in some embodiments, the compounds of Formula I have potent anticancer activity.

When Y is C═C, the compounds of Formula I tend to be more active as HDAC inhibitors. Without wishing to be bound by theory, it is believed that this is because the double bond in the Y position causes the compounds to keep their shape better than a single bond in a Y position. Furthermore, it has been found that electron withdrawing groups at the $R_2$ position result in greater activity. For example, when $R_2$ is a fluorophenyl group or a trifluoromethylphenyl group, the compounds tend to have increased HDAC inhibition activity.

Where each X is O, and Y is C═C, the compounds have the following general Formula II:

Formula II

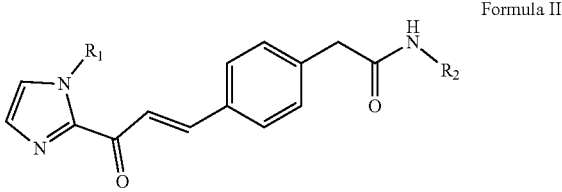

where $R_1$ is hydrogen, alkyl, aryl, heteroaryl, aralkyl, or heteroaralkyl; and $R_2$ is hydrogen, alkyl, aryl, heteroaryl, aralkyl, or heteroaralkyl.

Where each X is O, and $R_1$ is H, the compounds have the following general Formula III:

Formula III

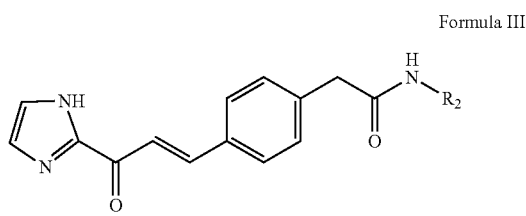

where $R_2$ is hydrogen, alkyl, aryl, heteroaryl, aralkyl, or heteroaralkyl.

Where each X is O, and Y is a cyclopropyl ring, the compounds have the following general Formula IV:

Formula IV

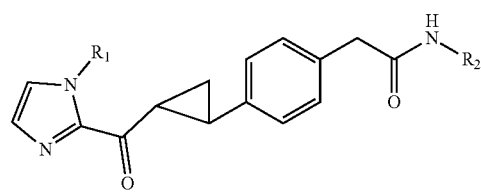

where $R_1$ is hydrogen, alkyl, aryl, heteroaryl, aralkyl, or heteroaralkyl; and $R_2$ is hydrogen, alkyl, aryl, heteroaryl, aralkyl, or heteroaralkyl.

When one X is S, and the other X is O, the compounds can have the following general Formula V:

Formula V

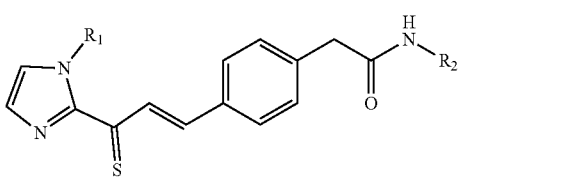

where $R_1$ is hydrogen, alkyl, aryl, heteroaryl, aralkyl, or heteroaralkyl; and $R_2$ is hydrogen, alkyl, aryl, heteroaryl, aralkyl, or heteroaralkyl.

When each X is S, the compounds have the following general Formula VI:

Formula VI

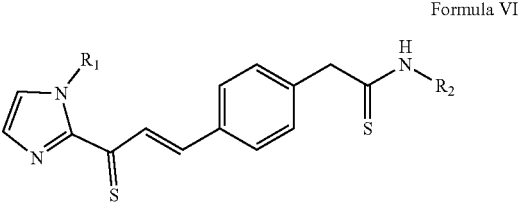

where $R_1$ is hydrogen, alkyl, aryl, heteroaryl, aralkyl, or heteroaralkyl; and $R_2$ is hydrogen, alkyl, aryl, heteroaryl, aralkyl, or heteroaralkyl.

As noted, for any of the compounds of Formula I, either of $R_1$ and $R_2$ can be hydrogen, alkyl, aryl, heteroaryl, aralkyl, or heteroaralkyl. In some embodiments, either of $R_1$ or $R_2$ is H, alkyl, substituted or unsubstituted phenyl, cyclohexyl, or napthalyl. Suitable $R_1$ and $R_2$ groups include, but are not limited to: H, methyl, ethyl, phenyl, naphthalyl, 4-dimethylaminophenyl, 4-methoxyphenyl, p-tolyl, 4-fluorophenyl, cyclohexyl, 4-trifluoromethylphenyl, and 4-chlorophenyl.

One non-limiting example compound of Formula I is compound 17, which is also known as (E)-2-(4-(3-(1H-imidazol-2-yl)-3-oxoprop-1-en-1-yl)phenyl)-N-(naphthalen-1-yl)acetamide, and has the following structure:

17

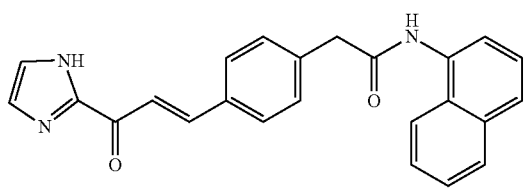

Another non-limiting example compound of Formula I is compound 18, which is also known as (E)-2-(4-(3-(1H-imidazol-2-yl)-3-oxoprop-1-en-1-yl)phenyl)-N-(4-(dimethylamino)phenyl) acetamide, and has the following structure:

18

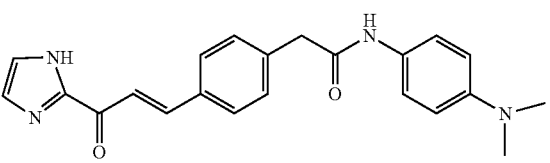

Another non-limiting example compound of Formula I is compound 19, which is also known as (E)-2-(4-(3-(1H-imidazol-2-yl)-3-oxoprop-1-en-1-yl)phenyl)-N-(4-methoxyphenyl) acetamide, and has the following structure:

19

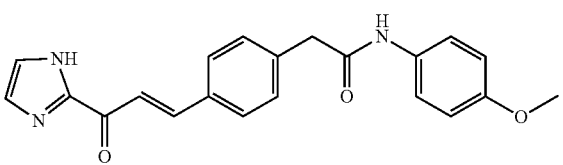

Another non-limiting example compound of Formula I is compound 20, which is also known as (E)-2-(4-(3-(1H-imidazol-2-yl)-3-oxoprop-1-en-1-yl)phenyl)-N-(p-tolyl)acetamide, and has the following structure:

20

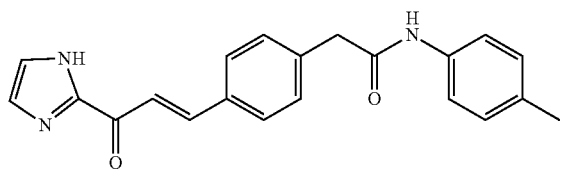

Another non-limiting example compound of Formula I is compound 21, which is also known as (E)-2-(4-(3-(1H-imidazol-2-yl)-3-oxoprop-1-en-1-yl)phenyl)-N-phenylacetamide, and has the following structure:

21

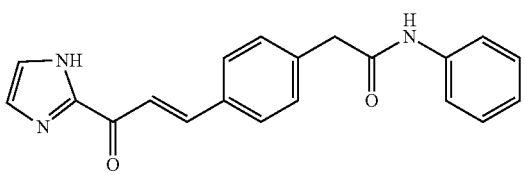

Another non-limiting example compound of Formula I is compound 22, which is also known as (E)-2-(4-(3-(1H-imidazol-2-yl)-3-oxoprop-1-en-1-yl)phenyl)-N-(4-fluorophenyl)acetamide, and has the following structure:

22

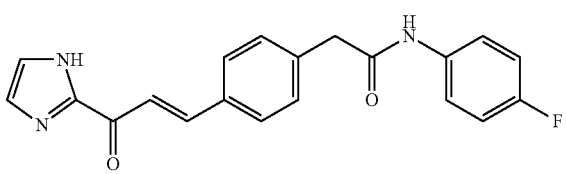

Another non-limiting example compound of Formula I is compound 23, which is also known as (E)-2-(4-(3-(1H-imidazol-2-yl)-3-oxoprop-1-en-1-yl)phenyl)-N-cyclohexylacetamide, and has the following structure:

23

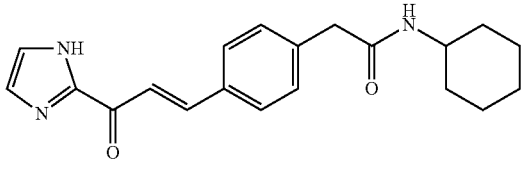

Another non-limiting example compound of Formula I is compound 24, which is also known as (E)-2-(4-(3-(1H-imidazole-2-yl)-3-oxoprop-1-en-1-yl)phenyl)-N-(4-(trifluoromethyl)phenyl) acetamide, and has the following structure:

24

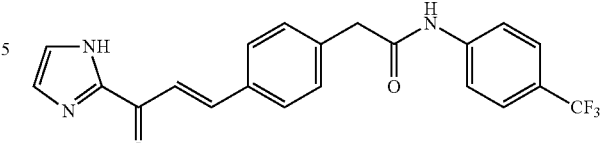

Another non-limiting example compound of Formula I is compound 25, which is also known as (E)-2-(-4 (3-(1H-imidazol-2-yl)-3-oxoprop-1-en-1-yl)phenyl)-N-(4-chlorophenyl)acetamide, and has the following structure:

25

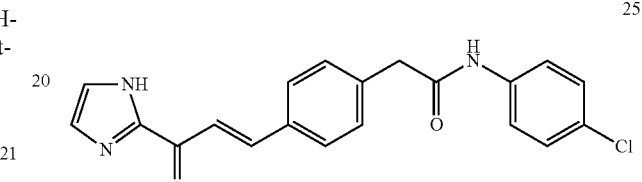

Another non-limiting example compound of Formula I is compound 26, which is also known as (E)-2-(4-(3-(1-methyl-1H-imidazol-2-yl)-3-oxoprop-1-en-1-yl)phenyl)-N-(4-(trifluoromethyl)phenyl) acetamide, and has the following structure:

26

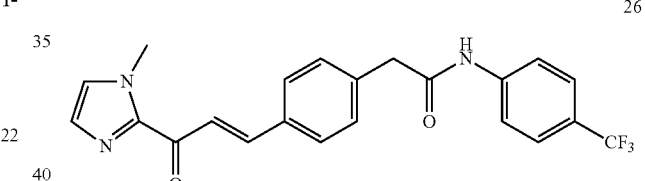

Another non-limiting example compound of Formula I is compound 27, which is also known as (E)-2-(4-(3-(1-methyl-1H-imidazol-2-yl)-3-oxoprop-1-en-1-yl)phenyl)-N-phenylacetamide, and has the following structure:

27

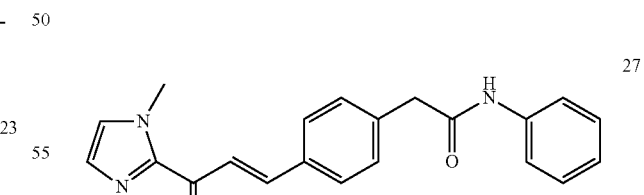

Another non-limiting example compound of Formula I is compound 28, which is also known as (E)-N-(4-fluorophenyl)-2-(4-(3-(1-methyl-1H-imidazol-2-yl)-3-oxoprop-1-en-1-yl)phenyl)acetamide, and has the following structure:

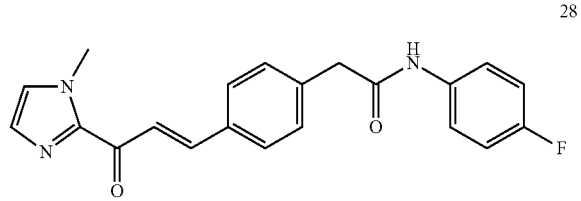 [SMILES: Cn1ccnc1C(=O)/C=C/c1ccc(CC(=O)Nc2ccc(F)cc2)cc1]

28

Another non-limiting example compound of Formula I is compound 29, which is also known as (E)-N-cyclohexyl-2-(4-(3-(1-methyl-1-H-imidazol-2-yl)-3-oxoprop-1-en-1-yl) phenyl) acetamide, and has the following structure:

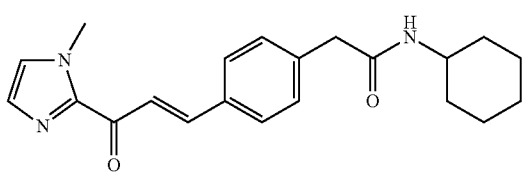

29

Another non-limiting example compound of Formula I is compound 30, which is also known as (E)-N-(4-chlorophenyl)-2-(4-(3-(1-methyl-1H-imidazol-2-yl)-3-oxoprop-1-en-1-yl) phenyl)acetamide, and has the following structure:

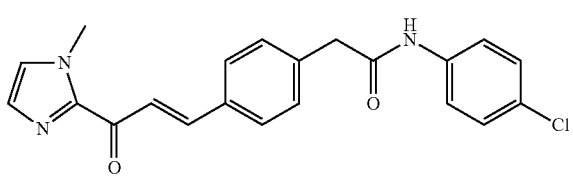

30

Another non-limiting example compound of Formula I is compound 31, which is also known as (E)-2-(4-(3-(1-ethyl-1H-imidazol-2-yl)-3-oxoprop-1-en-1-yl)phenyl)-N-(4-fluorophenyl)acetamide, and has the following structure:

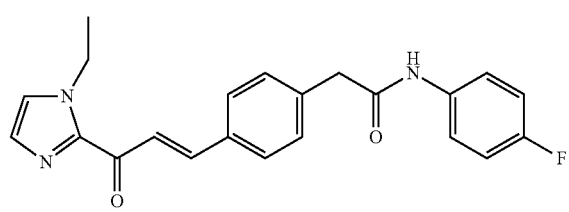

31

Another non-limiting example compound of Formula I is compound 32, which is also known as 2-(4-(3-(1H-imidazol-2-yl)-3-oxopropyl)phenyl)-N-phenylacetamide, and has the following structure:

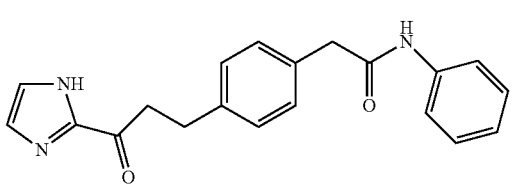

32

In another non-limiting example, the compound comprises (E)-2-(4-(3-(1H-imidazol-2-yl)-3-oxoprop-1-en-1-yl) phenyl)-N-(3,4,5-trifluorophenyl) acetamide 33

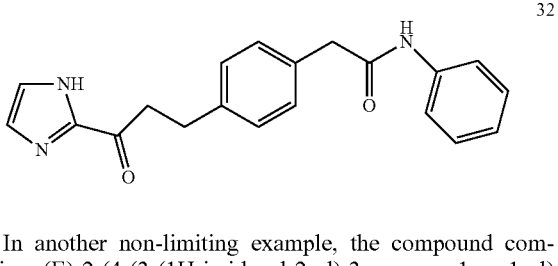

33

In another non-limiting example, the compound comprises (E)-2-(4-(3-(1-methyl-1H-imidazol-2-yl)-3-oxoprop-1-en-1-yl) phenyl)-N-(3,4,5-trifluorophenyl)acetamide 34

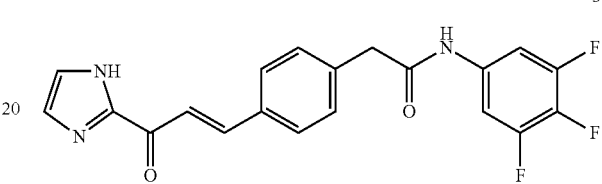

34

In another non-limiting example, the compound comprises (E)-2-(4-(3-(1H-imidazol-2-yl)-3-oxoprop-1-en-1-yl) phenyl)-N-(perfluorophenyl)acetamide 35

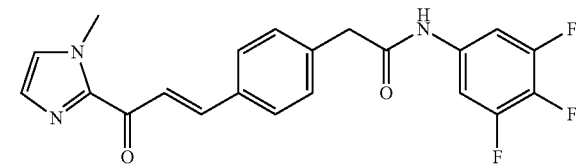

35

In another non-limiting example, the compound comprises (E)-2-(4-(3-(1-methyl-1H-imidazol-2-yl)-3-oxoprop-1-en-1-yl) phenyl)-N-(perfluorophenyl)acetamide 36

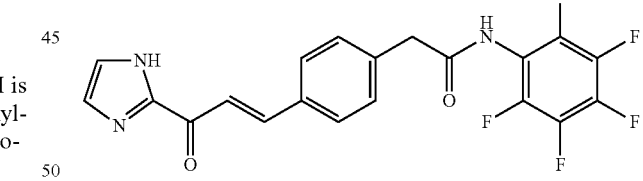

36

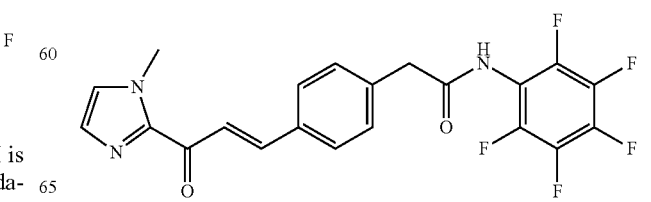

In another non-limiting example, the compound comprises (E)-2-(4-(3-(1H-imidazol-2-yl)-3-oxoprop-1-en-1-yl)phenyl)-N-(3,5-bis(trifluoromethyl)phenyl) acetamide 37

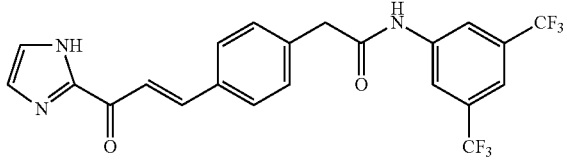

In another non-limiting example, the compound comprises (E)-N-(3,5-Bis(trifluoromethyl)phenyl)-2-(4-(3-(1-methyl-1H-imidazol-2-yl)-3-oxoprop-1-en-1-yl) phenyl) acetamide 38

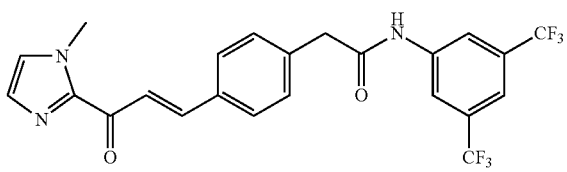

In another non-limiting example, the compound comprises 39

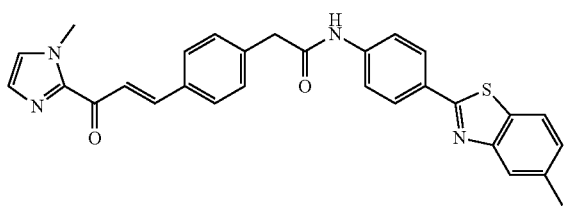

In another non-limiting example, the compound comprises 40

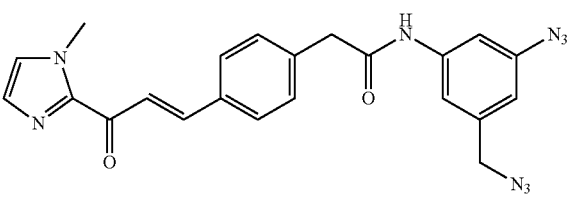

In another non-limiting example, the compound comprises 41

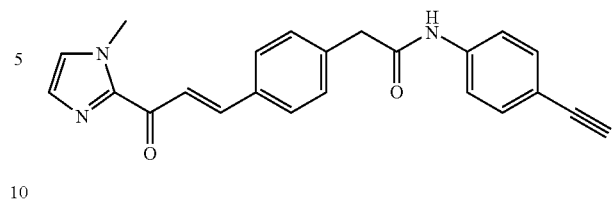

Figure 2:
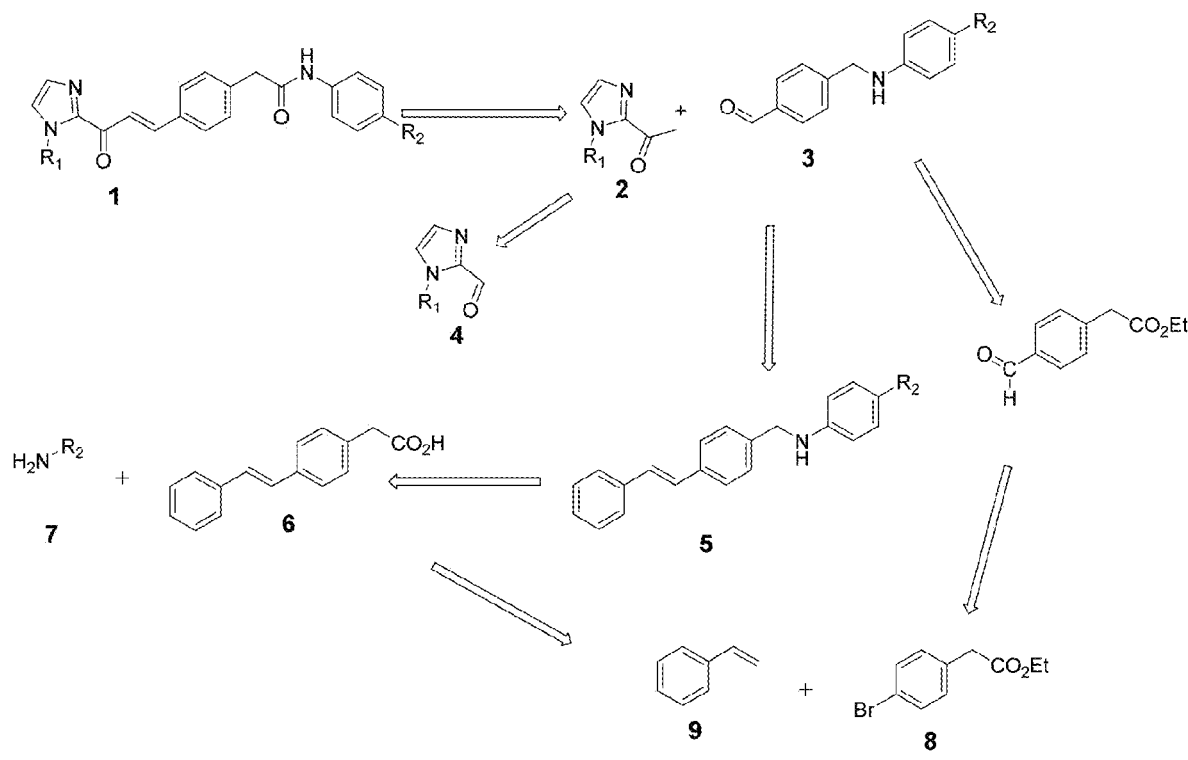
FIG. 2: Scheme depicting a non-limiting example synthesis of HDAC inhibitors.

The synthesis of the HDAC inhibitors is depicted in Schemes shown in FIGS. 2-5. As depicted in FIG. 2, the 1-(1H-imidazol-2-yl)ethan-1-one containing compounds can be synthesized by aldol reaction of tosyl-protected imidazole ketone 2 with aldehydes 3. The aldehydes 3 can be obtained by Heck coupling of bromoester 8 with styrene 9 followed by ester hydrolysis, amide formation, and oxidative cleavage of olefinic double bond. It can also be obtained by direct carbonylation of the bromoester 8, followed by ester hydrolysis and amide formation.

Figure 3A:
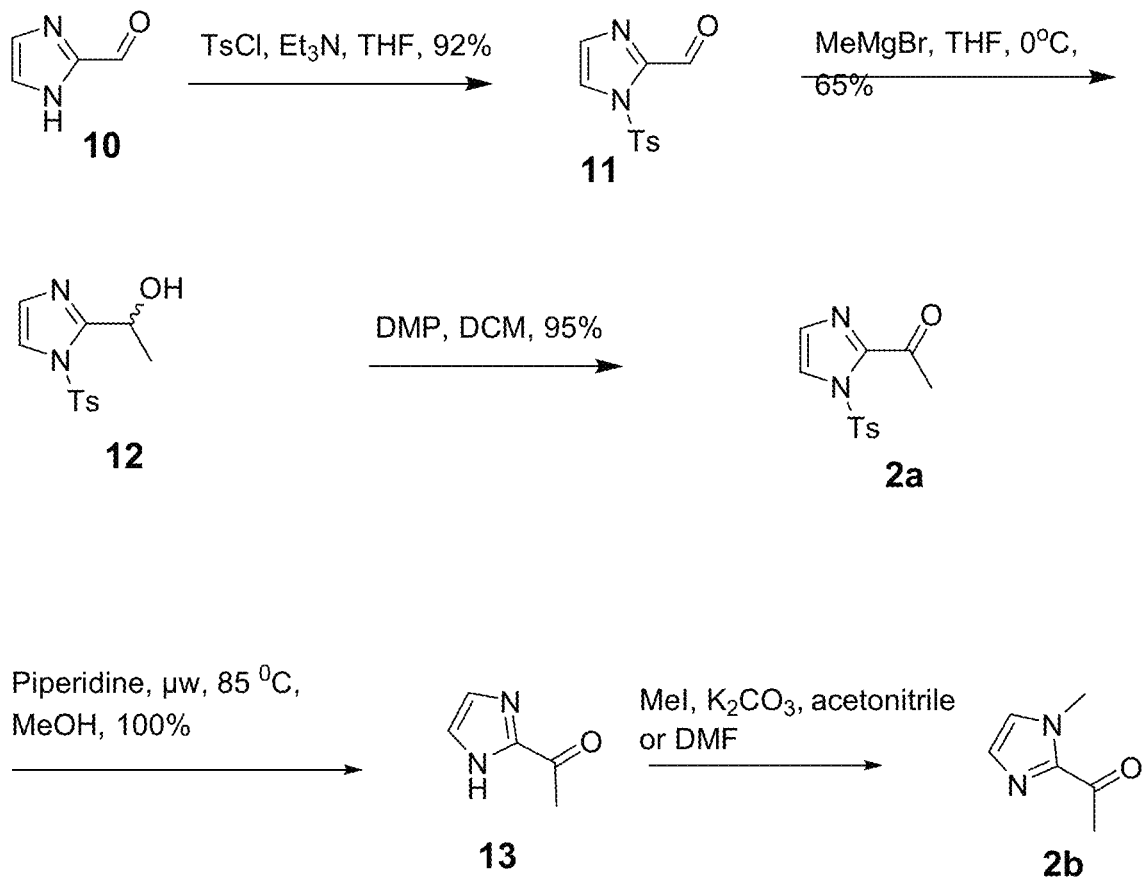
FIG. 3A: Scheme depicting a non-limiting example synthesis of the zinc-binding moiety.

The 1-(1H-imidazol-2-yl)ethan-1-one moiety can be synthesized as shown for the imidazole ketone 2a in Scheme in FIG. 3A. 1-H-imidazole-2-caroxaldehyde 10 can be tosylated to produce aldehyde 11, which can then be treated with MeMgBr, followed by Dess-Martin periodinane oxidation, to afford the tosyl imidazole ketone 2a. The tosyl group of 2a can be removed by heating with piperidine in anhydrous methanol at 85° C. for many hours, or by heating at 85° C. for 4 hours in a microwave synthesizer, followed by N-alkylation using methyl iodide in the presence of potassium carbonate in anhydrous acetonitrile or DMF to give the N-methyl ketone 2b.

Figure 3B:
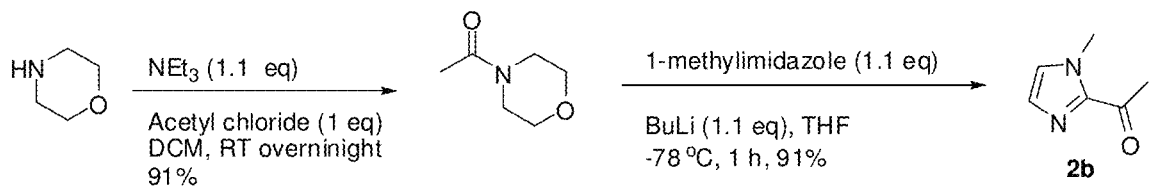
FIG. 3B: Scheme depicting a non-limiting example synthesis of making compound 2b.

Alternative method for making intermediate 2b is shown in FIG. 3B, N-methyl imidazole ketone 2b was also made as described by Duchemin et al. (Duchemin, N.; Benedetti, E.; Bethge, L.; Vonhoff, S.; Klussmann, S.; Vasseur, J.-J.; Cossy, J.; Smietana, M.; Arseniyadis, S. Expanding Biohybrid-Mediated Asymmetric Catalysis into the Realm of RNA. Chem. Commun. 2016, 52 (55), 8604-8607).

Palladium-catalyzed Heck coupling between styrene 9 and bromoester 8 produces the alkene 14, which can be saponified and subjected to amide coupling with amines 7a-7i to produce amides 15a-15i. These can be subjected to oxidative cleavage using osmium tetroxide and sodium periodate to produce aldehydes 16a-16i (Scheme in FIG. 4A).

Figure 4A:
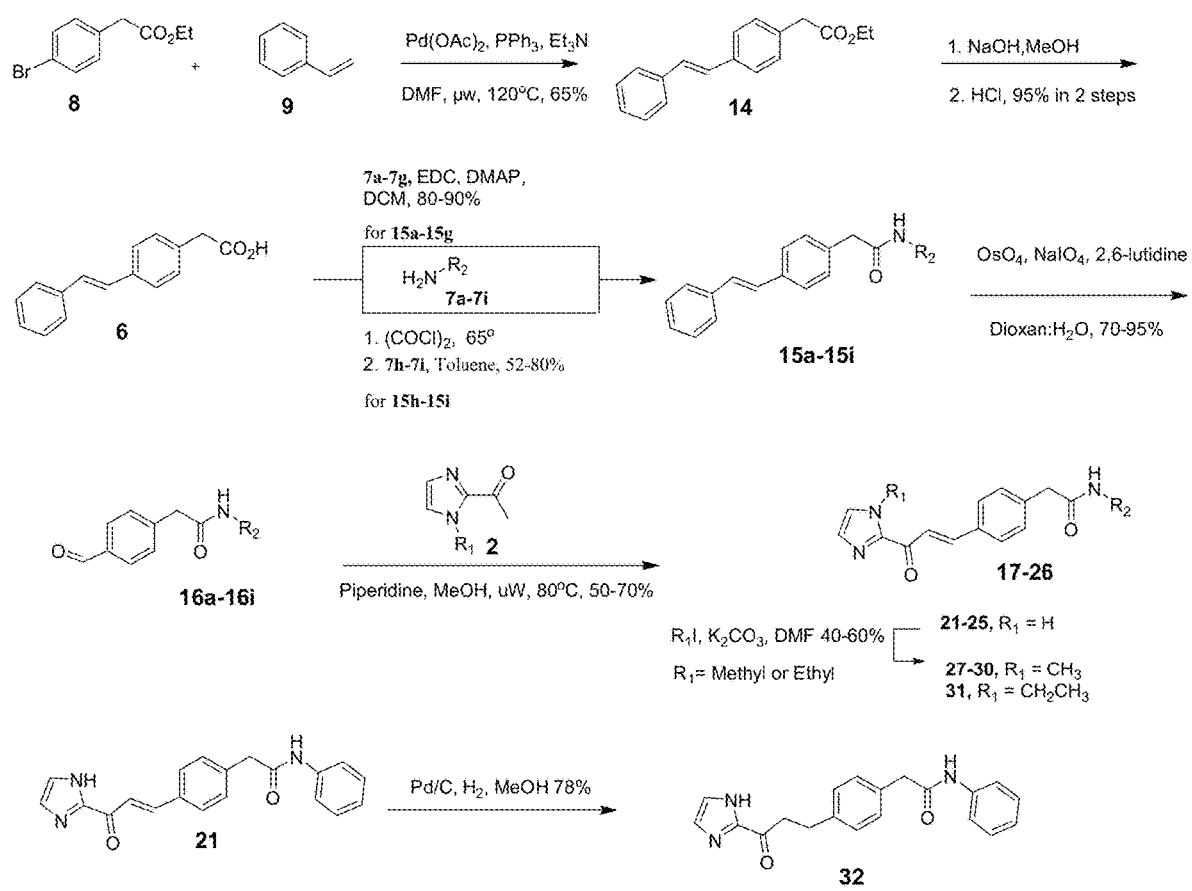
FIG. 4A: Scheme depicting a non-limiting example synthesis of HDAC inhibitors.

With both aldehydes 16a-16i and ketones 2a in hand, aldol reaction and tosyl group removal can be carried out in one step by heating with piperidine to produce the final products 17-26 in 50-70% yield (Scheme in FIG. 4A). Aldol reaction using ketone 2b or alkylation of the final products obtained with 2a produces the N1 alkylated analogs 27-31 (Scheme in FIG. 4A). Palladium-catalyzed hydrogenation of 21 give 32 (Scheme in FIG. 4A).

Figure 4B:
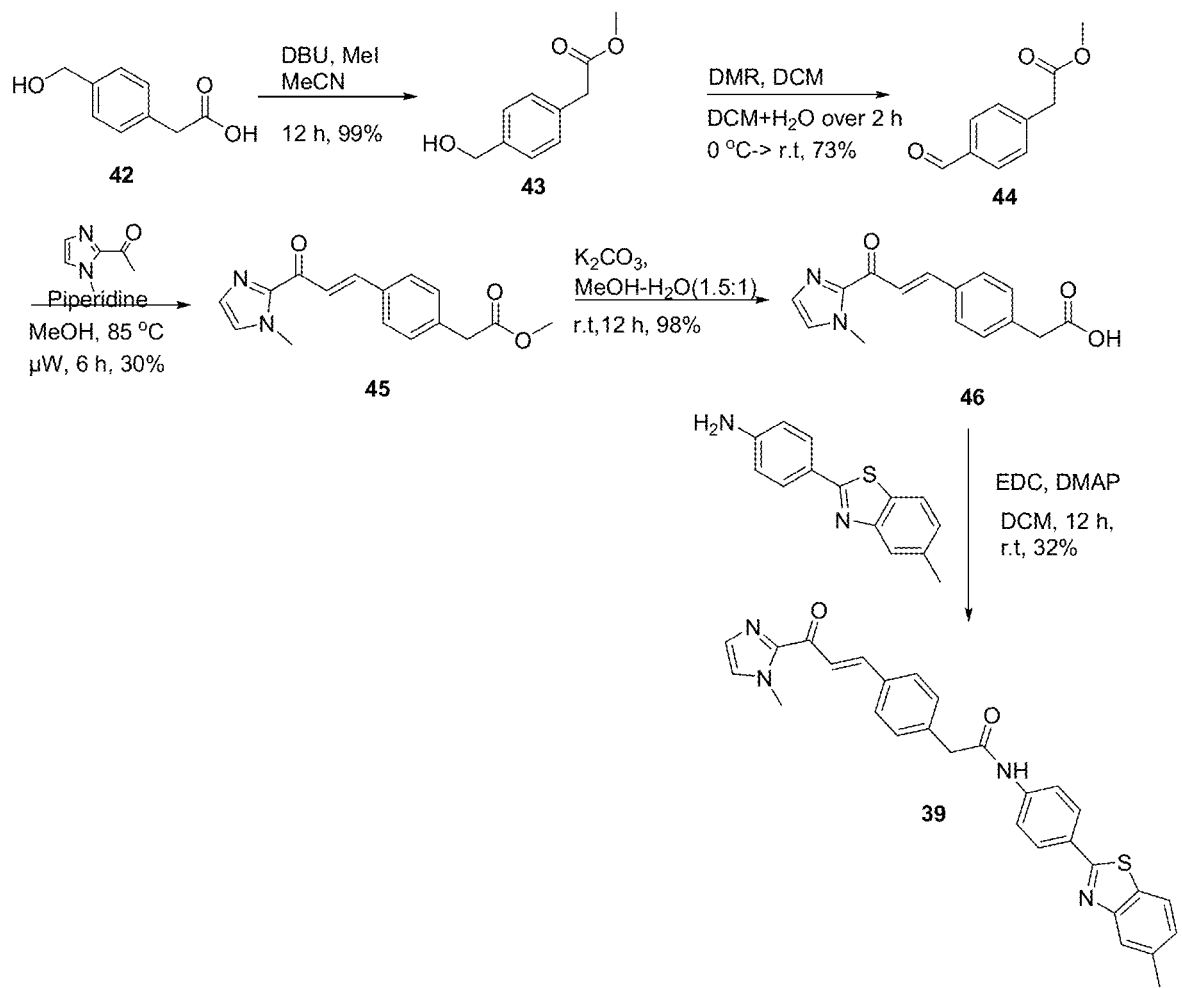
FIG. 4B: Scheme depicting alternative method of synthesizing the final analogues.
Figure 4C:
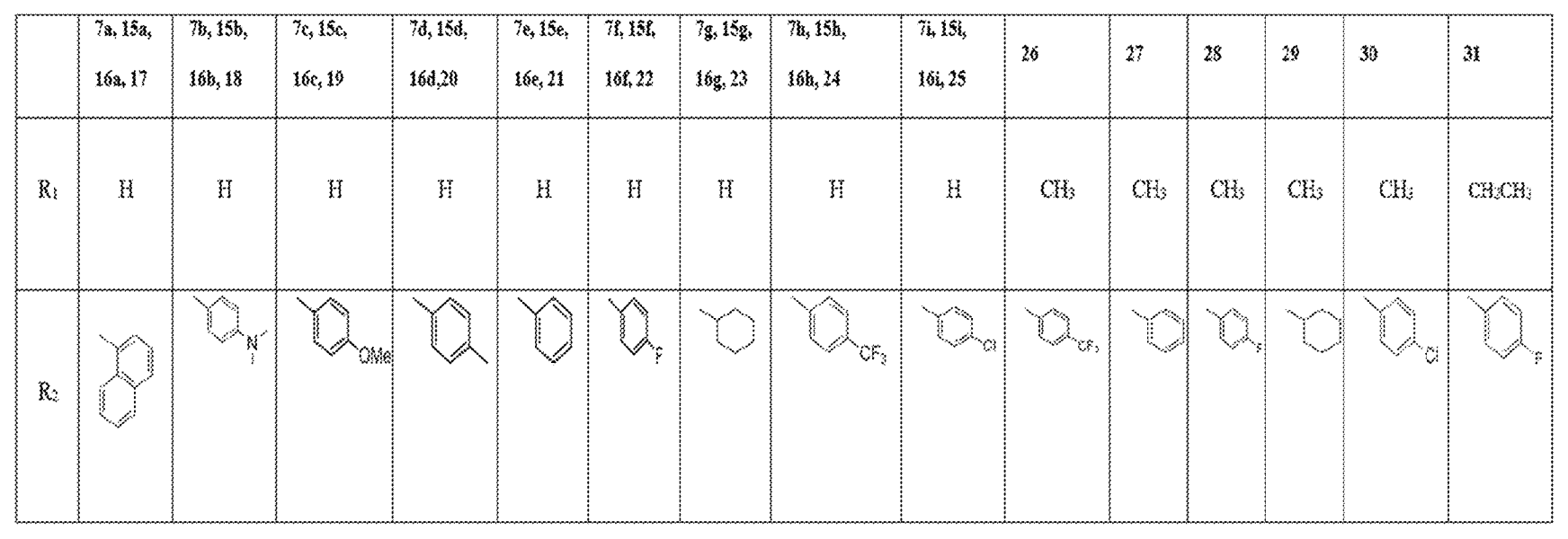

FIG. 4B shows alternative method of synthesizing the final analogues.

Figure 5:
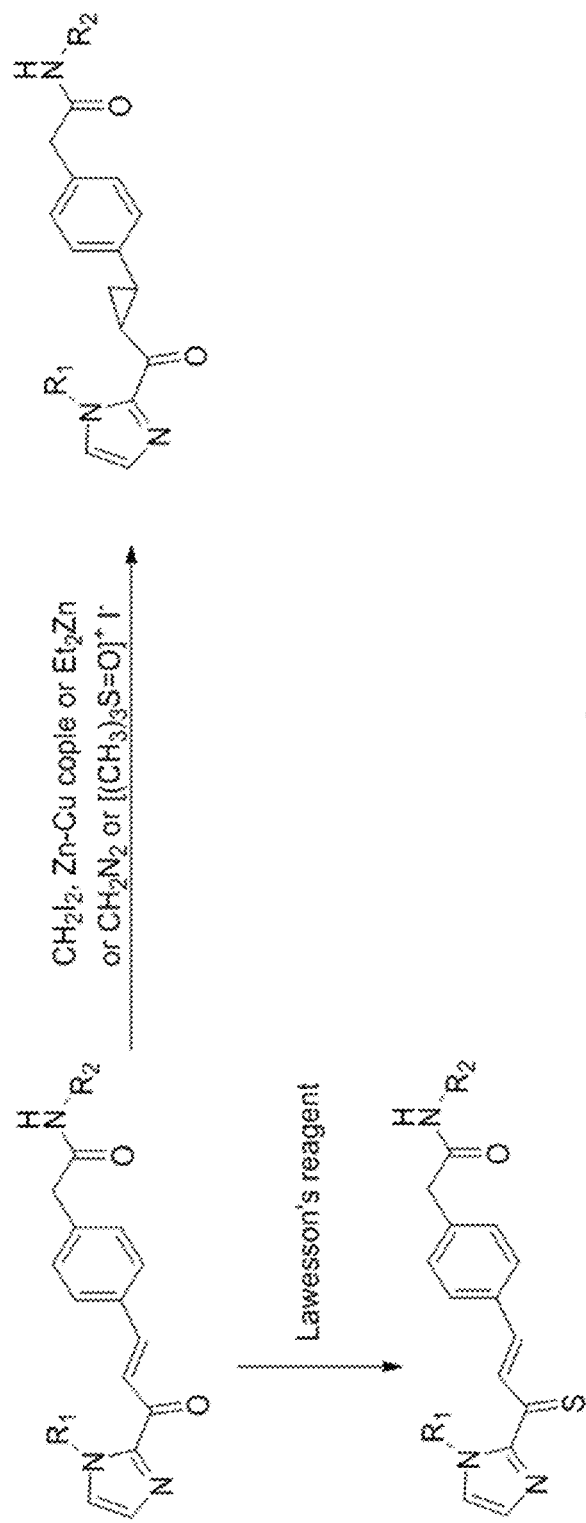
FIG. 5: Scheme depicting a non-limiting example synthesis of cyclopropyl and thioketone derivatives.

The final products 17-21 can be converted to the corresponding 1-(1H-imidazol-2-yl)ethane-1-thione by reaction with Lawesson's reagent (Scheme in FIG. 5). These can also be converted to the corresponding cyclopropyl derivatives by cyclopropanation with carbenoid reagents, iodomethylzinc iodide, diazomethane, and trimethylsulfoxonium iodide.

Pharmaceutical compositions of the present disclosure comprise an effective amount of an HDAC inhibitor compound disclosed herein (i.e., a compound of Formula I), and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/ body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

In particular embodiments, the compounds and compositions described herein are useful for treating various cancers such as, but not limited to: leukemia, non-small cell lung cancer, colon cancer, CNS cancer, melanoma, ovarian cancer, renal cancer, prostate cancer, and breast cancer. Furthermore, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, the HDAC inhibitor compounds or compositions can be administered in combination with one or more suitable anti-cancer agents including, but not limited to: chemotherapeutic agents; cytotoxins; antimetabolites; alkylating agents; protein kinase inhibitors; anthracyclines; antibiotics; miRNAs; anti-miRNAs; antimitotic agents (e.g. antitubulin agents); corticosteroids; radiopharmaceuticals; proteins such as cytokines, enzymes, or interferons; biological response modifiers such as krestin, lentinan, sizofiran, picibanil, ubenimex; anti-angiogenic compounds such as acitretin, fenretinide, thalidomide, zoledronic acid, angiostatin, aplidine, cilengtide, combretastatin A-4, endostatin, halofuginone, rebimastat, Removab®, Revlimid®, squalamine, ukrain, or Vitaxin®; platinum-coordinated compounds such as cisplatin, carboplatin, nedaplatin, or oxaliplatin; camptothecin derivatives such as camptothecin, 10-hydroxycamptothecin, 9-aminocamptothecin, irinotecan, SN-38, edotecarin, or topotecan; compounds or chelates that include radionuclides; or combinations thereof. Examples of suitable interferons include, but are not limited to interferon alpha, interferon alpha-2a, interferon, alpha-2b, interferon beta, interferon gamma-1a, interferon gamma-1b (Actimmune), interferon gamma-n1, or combinations thereof.

In certain embodiments, the anti-cancer agent is one or more of hydroxyureas, Taxol®, adriamycin, 5-fluorouracil, cyclophosphamide, etoposide, altretamine, ifosfamide, vinblastine sulfate, estramusiine phosphate, suramin, strontium-89, filgrastim, lentinan, sizofilan, TheraCys®, ubenimex, WF-10, aldesleukin, alemtuzumab, BAM-002, dacarbazine, daclizumab, denileukin, gemtuzumab ozogamicin, ibritumomab, imiquimod, lenograstim, lentinan, Corixa, molgramostim, OncoVAX-CL, sargramostim, tasonermin, tecleukin, thymalasin, tositumomab, Virulizin®, Z-100, epratuzumab, mitumomab, oregovomab, pemtumomab (Y-muHMFGI), Provenge® (Dendreon), alitretinoin, ampligen, atrasentan bexarotene, bortezomib, bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, Telcyta® (TLK-286, Telik Inc.), Velcade® (bortemazib, Millenium), or tretinoinor.

Another non-limiting example of a combination therapy for cancers or other diseases is the combination of HDAC inhibitor compounds or HDAC inhibitor compound-containing composition with one or more surgical treatments. Suitable surgical treatments include, but are not limited to, a polypectomy, a colectomy, a transanal resection, a wedge resection, a lobectomy, a pneumonectomy, a sleeve reduction, a hysterectomy, a bilaterial salpingo-oophorectomy, an omentectomy, or a nephrectomy. Other possible therapies suitable for combination with a HDAC inhibitor compound or HDAC inhibitor compound-containing composition include, but are not limited to, immunotherapy, hormone therapy, radiation therapy, or a combination thereof.

The HDAC inhibitor compounds described herein are also useful for disrupting chromosome alignment in a cell. Furthermore, the HDAC inhibitor compounds described herein are useful, in combination with an Aurora kinase inhibitor, for obliterating proper spindle function in a cell. Thus, another non-limiting example of a combination therapy with the HDAC inhibitor compounds is with an Aurora kinase inhibitor, such as, but not limited to, ZM447439.

Embodiments of the present disclosure further include methods of determining coverage or denial of health insurance reimbursement and/or payment for treatments of disease comprising the compounds or compositions described herein. In certain embodiments, the treatment comprises an HDAC inhibitor compound or HDAC inhibitor compound-containing pharmaceutical composition, and a provider of health insurance denies coverage or reimbursement for the treatment.

Kits

It is envisioned that the compounds, compositions, and methods described herein could be embodied as parts of a kit or kits. A non-limiting example of such a kit is a kit for making a HDAC inhibitor compound, the kit comprising an aldehyde and a tosyl-protected imidazole ketone in separate containers, where the containers may or may not be present in a combined configuration. Many other kits are possible, such as kits further comprising one or more reagents selected from piperidine, or other reagents for converting an HDAC inhibitor compound to a corresponding thione, N1 alkylated analog, or cyclopropyl derivative, or kits further comprising a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

As noted, the HDAC inhibitor compounds described herein are useful anticancer agents. However, it is possible that the HDAC inhibitor compounds also act by mechanisms in addition to HDAC inhibition, and therefore are useful for other therapeutic purposes as well. For example, as shown in the Examples herein, the HDAC inhibitor compounds cause cells to become rounded but not get out of mitosis. In addition, the HDAC inhibitor compounds are useful agents for analyzing mechanisms of cell death because they are relatively easy to make and can readily kill certain cells.

EXAMPLES

Compounds were prepared as shown in Scheme in FIGS. 2-5.

Synthesis of 1H-imidazole Ketones

1-Tosyl-1H-imidazole-2-carbaldehyde 11

To a stirred solution of 1H-imidazole-2-carbaldehyde 10 (1.92 g, 20 mmol, 1 eq) in dichloromethane (40 mL) were added tosyl chloride (4.2 g, 22 mmol, 1.1 eq), triethylamine (4.05 g, 40 mmol, 2 eq), and DMAP (244 mg, 2 mmol, 0.1 equiv). The reaction mixture was stirred overnight at room temperature. The solvent was evaporated under reduced pressure. The residue was purified by column chromatography on silica gel in 40% ethyl acetate in hexanes to give 11 as an off-white powder (3.8 g, 76%); mp 155° C. $^1$H NMR (600 MHz, CDCl$_3$) δ 9.81 (s, 1H), 8.02 (d, J=8.4 Hz, 2H), 7.86 (s, 1H), 7.39 (d, J=8.5 Hz, 2H), 7.33 (d, J=1.3 Hz, 1H), 2.47 (s, 3H). $^{13}$C NMR (151 MHz, CDCl$_3$) δ 178.71, 146.88, 143.55, 133.68, 130.54, 130.03, 128.93, 124.65, 21.84.

1-(1-Tosyl-1H-imidazol-2-yl)ethan-1-ol 12

To a stirred solution of 1-tosyl-1H-imidazole-2-carbaldehyde 11 (1.1 g, 4.4 mmol, 1 eq) in tetrahydrofuran (15 mL) at −78° C. was added methyl magnesium bromide (8.8 mL of 1.0 M solution in butyl ether, 8.8 mmol, 2 eq). The reaction mixture was stirred for 1 h at −78° C. After adding saturated ammonium chloride (10 mL), the reaction mixture was extracted with ethyl acetate (20 mL). The organic layer was separated, and the water layer was extracted with ethyl acetate (3×10 mL). The combined organic extract was washed with brine and dried over anhydrous sodium sulfate and the solvent was evaporated under reduced pressure. The residue was purified by column chromatography on silica gel in ethyl acetate/hexanes (30-60%) to give 12 as a yellow oil (750 mg, 65%), recovered starting material (190 mg, 18%); mp 199-200° C. $^1$H NMR (400 MHz, CDCl$_3$) δ 7.77 (d, J=8.3 Hz, 2H), 7.31 (dd, J=18.8, 4.9 Hz, 3H), 6.89 (d, J=1.5 Hz, 1H), 5.20 (q, J=6.5 Hz, 1H), 2.36 (s, 3H), 1.51 (d, J=6.5 Hz, 3H). $^{13}$C NMR (151 MHz, CDCl$_3$) δ 151.90, 146.40, 134.98, 130.43, 128.19, 127.38, 119.89, 63.00, 22.25, 21.76. HRMS: (ESI) calcd for C$_{12}$H$_{14}$N$_2$O$_3$S [M+H]$^+$ 267.0803; found, 267.0797.

1-(1-Tosyl-1H-imidazol-2-yl)ethan-1-one 2a

To a stirred solution of 1-(1-tosyl-1H-imidazol-2-yl) ethan-1-ol 12 (535 mg, 2 mmol, 1 eq) in dichloromethane (25 mL) at 0° C. was added Dess-Martin Periodinane (1.02 g, 2.4 mmol, 1.2 eq). The reaction mixture was stirred for 4 h at room temperature, filtered through a pad of celite, and concentrated in vacuo. The residue was purified by column chromatography on silica gel in ethyl acetate/hexanes (5-20%) to give 2a as an off-white powder (528 mg, 100%); mp 103-104° C. $^1$H NMR (400 MHz, CDCl$_3$) δ 7.98 (t, J=8.1 Hz, 6H), 7.87 (d, J=1.3 Hz, 3H), 7.36 (d, J=8.1 Hz, 7H), 7.18 (d, J=1.3 Hz, 3H), 2.58 (s, 9H), 2.44 (s, 9H). $^{13}$C NMR (151 MHz, CDCl$_3$) δ 187.71, 146.14, 143.96, 134.25, 129.98, 129.62, 129.10, 128.43, 127.41, 124.99, 44.64, 27.23, 21.82.

1-(1H-Imidazol-2-yl)-ethan-1-one 13

To 1-(1-tosyl-1H-imidazole-2-yl)-ethan-1-one 2a (0.2 g, 0.76 mmol, 1.0 equiv) in a microwave vial under nitrogen were added piperidine (300 µL 3.04 mmol, 4.0 equiv) and anhydrous methanol (5.0 mL). The reaction mixture was heated in the microwave synthesizer 85° C. for 4 h and monitored by TLC (50% ethyl acetate-hexanes). Methanol was removed on a rotary evaporator to obtain a brown oil. It was chromatographed on silica gel in 30-50% ethyl acetate/hexanes to yield 1-(1H-imidazol-2-yl)ethan-1-one 13 as a clear oil (75 mg, 89%). TLC R$_f$=0.4 (50% ethyl acetate/hexanes), $^1$H NMR (600 MHz, CDCl$_3$) δ 7.30 (s, 1H), 7.25 (d, J=1.3 Hz, 1H), 2.68 (s, 3H), 1.62 (s, 2H) ppm. $^{13}$C NMR (151 MHz, CDCl$_3$) δ 189.52, 131.49, 120.07, 25.40 ppm.

1-(1-Methyl-1H-imidazol-2-yl)ethan-1-one 2b

To a mixture of 1-(1H-imidazol-2-yl)ethan-1-one 13 (75 mg, 0.68 mmol, 1.0 equiv) and potassium carbonate (235 mg, 1.7 mmol, 2.5 equiv) under nitrogen were added methyl iodide (47 µL 0.7 mmol, 1.1 equiv) and anhydrous acetonitrile (1.0 mL) via syringe. The reaction mixture was stirred overnight at room temperature and monitored by TLC (1.0% methanol/DCM). Acetonitrile was removed on rotary evaporator and the residue was treated with water (5.0 mL) and extracted with DCM (3×5.0 mL). The combined organic extract was dried over anhydrous sodium sulfate and concentrated on rotary evaporator to obtain a brown oil. It was chromatographed on silica gel in 0.5-1 methanol/DCM to yield 1-(1-methyl-1H-imidazol-2-yl)ethan-1-one 2a as clear oil (22 mg, 26%). TLC R$_f$=0.25 (1% methanol/DCM), $^1$H NMR (600 MHz, CDCl$_3$) δ 7.16 (s, 1H), 7.05 (s, 1H), 4.02 (s, 1H), 2.69 (s, 1H), 1.61 (s, 1H) ppm. $^{13}$C NMR (151 MHz, CDCl$_3$) δ 190.72, 143.28, 131.46, 129.08, 126.98, 36.27, 27.20, 25.39 ppm. HRMS calcd for C$_6$H$_9$N$_2$O: 125.0714, found: 125.0754.

Ethyl (E)-2-(4-styrylphenyl)acetate 14

To a solution of ethyl 2-(4-bromophenyl)acetate 8 (2.4 g, 10 mmol, 1 equiv) in dimethylformamide (10 mL) in a microwave vial was added styrene 9 (1.041 g, 30 mmol, 3 equiv), palladium acetate (80 mg, 3 mole %), triphenyl phosphine (160 mg, 6 mole %), and trimethylamine (2.024 mL, 20 mmol, 2 equiv). The reaction mixture was heated in a microwave synthesizer for 6 h at 120° C. It was allowed to cool to room temperature. The resulting suspension was filtered and the filtrate was concentrated under reduced pressure. The residue was purified by column chromatography on silica gel in ethyl acetate/hexanes (1-3%) to afford 14 as a white powder (1.73 g, 65%); mp 72° C. $^1$H NMR (400 MHz, CDCl$_3$) δ 7.55-7.44 (m, 2H), 7.36 (t, J=7.6 Hz, 1H), 7.28 (dd, J=6.3, 4.4 Hz, 1H), 7.10 (d, J=8.7 Hz, 1H), 4.22-4.07 (m, 1H), 3.62 (s, 1H), 1.26 (td, J=7.1, 3.2 Hz, 1H). $^{13}$C NMR (151 MHz, CDCl$_3$) δ 171.55, 137.30, 136.21, 133.52, 129.61, 128.70, 128.64, 128.26, 127.64, 126.69, 126.51, 60.95, 41.21, 14.21. HRMS: (ESI) calcd for C$_{18}$H$_{18}$O$_2$ [M+H]$^+$ 267.1385; found, 267.1374.

(E)-2-(4-Styrylphenyl)acetic acid 6

To a stirred solution of ethyl (E)-2-(4-styrylphenyl)acetate 14 (1.5 g, 6.25 mmol, 1 equiv) in methanol (15 mL) at 0° C. was added sodium hydroxide (375 mg, 9.4 mmole, 1.5 equiv). The reaction mixture was stirred at room temperature for 6 h, and acidified with hydrochloric acid. The solid product was collected by filtration and dried to afford 6 as a white powder (1.35 g, 91%); mp 195° C. $^1$H NMR (400 MHz, CDCl3) δ 7.49 (q, J=8.7 Hz, 2H), 7.36 (t, J=7.5 Hz, 1H), 7.27 (dd, J=12.0, 6.9 Hz, 2H), 7.10 (s, 1H), 3.67 (s, 1H). $^{13}$C NMR (151 MHz, CDCl$_3$) δ 137.24, 136.55, 132.59, 129.73, 128.87, 128.71, 128.13, 127.70, 126.78, 126.53, 40.51.

General Procedure for the Synthesis of Amides 15a-15g

To a stirred solution of (E)-2-(4-styrylphenyl)acetic acid 6 (1 equiv) in dichloromethane (20 mL) were added 1-ethyl-3-(3-dimethylaminopropyl)carbodiimide (1.5 equiv), DMAP (0.1 equiv), and amines 7a-7g (1.5 equiv). The reaction mixture was stirred at room temperature overnight. Water (10 mL) was added, the organic layer was separated, and the water layer was extracted with dichloromethane (3×10 mL). The combined organic extract was washed with brine and dried over anhydrous sodium sulfate, and the solvent was evaporated under reduced pressure. The residue was purified by column chromatography on silica gel in ethyl acetate/hexanes (10-30%) to give amides 15a-15g.

(E)-N-(Naphthalen-1-yl)-2-(4-styrylphenyl)acetamide 15a

Yellow powder (73%); mp 206° C. $^1$H NMR (600 MHz, CDCl$_3$) δ 7.94 (d, J=7.5 Hz, 1H), 7.80 (d, J=8.0 Hz, 1H), 7.64 (d, J=8.2 Hz, 1H), 7.61 (d, J=8.1 Hz, 2H), 7.52 (d, J=7.5 Hz, 2H), 7.43 (dd, J=13.3, 5.8 Hz, 4H), 7.36 (ddd, J=26.6, 15.4, 5.9 Hz, 5H), 7.26 (t, J=6.7 Hz, 1H), 7.14 (d, J=3.2 Hz, 2H), 3.89 (s, 2H). $^{13}$C NMR (151 MHz, CDCl$_3$) δ 169.44, 137.15, 137.05, 134.02, 133.80, 131.93, 130.16, 129.41, 128.80, 128.78, 127.91, 127.80, 127.53, 126.83, 126.60, 126.39, 125.93, 125.82, 125.76, 120.36, 119.99, 44.67. HRMS: (ESI) calcd for C$_{26}$H$_{21}$NO [M+H]$^+$ 364.1701; found, 364.1712.

(E)-N-(4-(Dimethylamino)phenyl)-2-(4-styrylphenyl)acetamide 15b

Off-white powder (73%); mp 229° C. $^1$H NMR (600 MHz, CDCl$_3$) δ 9.81 (s, 1H), 8.02 (d, J=8.4 Hz, 2H), 7.86 (s, 1H), 7.39 (d, J=8.5 Hz, 2H), 7.33 (d, J=1.3 Hz, 1H), 2.47 (s, 3H). $^{13}$C NMR (151 MHz, CDCl$_3$) δ 168.72, 137.15, 136.72, 134.00, 129.97, 129.13, 128.74, 127.95, 127.80, 127.25, 126.57, 121.84, 44.44. HRMS: (ESI) calcd for C$_{24}$H$_{24}$N$_2$O [M+H]$^+$ 357.1967; found, 357.1967.

(E)-N-(4-Methoxyphenyl)-2-(4-styrylphenyl)acetamide 15c

White powder (77%); mp 202-203° C. $^1$H NMR (400 MHz, CDCl$_3$) δ 7.54 (t, J=8.3 Hz, 4H), 7.41-7.28 (m, 7H), 7.13 (d, J=1.5 Hz, 2H), 6.94 (s, 1H), 6.85-6.79 (m, 2H), 3.77 (s, 3H), 3.74 (s, 2H). $^{13}$C NMR (151 MHz, CDCl$_3$) δ 168.80, 156.57, 137.11, 136.85, 133.74, 130.64, 129.96, 129.23, 128.75, 127.88, 127.84, 127.31, 126.57, 121.79, 114.09, 55.48, 44.45. HRMS: (ESI) calcd for C$_{23}$H$_{21}$NO$_2$ [M+H]$^+$ 344.1651; found, 344.1682.

(E)-2-(4-styrylphenyl)-N-(p-tolyl)acetamide 15d

White solid (80%); mp. 220° C., $^1$H NMR (600 MHz, CDCl$_3$) δ 7.55 (dd, J=12.0, 7.7 Hz, 1H), 7.38 (t, J=7.4 Hz, 1H), 7.34 (d, J=7.6 Hz, 1H), 7.32-7.28 (m, 1H), 7.14 (d, J=3.6 Hz, 1H), 7.09 (d, J=7.7 Hz, 1H), 6.99 (s, 1H), 3.75 (s, 1H), 2.30 (s, 1H), 1.57 (s, 1H) ppm. $^{13}$C NMR (151 MHz, CDCl$_3$) δ 168.81, 137.12, 136.84, 135.0, 134.18, 133.70, 129.96, 129.45, 129.22, 128.75, 127.86, 127.31, 126.57, 119.91, 44.59, 20.87 ppm.

(E)-N-Phenyl-2-(4-styrylphenyl)acetamide 15e

White powder (70%); mp 70° C. $^1$H NMR (400 MHz, CDCl3) δ 7.53 (dd, J=15.7, 7.4 Hz, 11H), 7.46 (t, J=8.1 Hz, 3H), 7.42 (d, J=7.9 Hz, 4H), 7.40-7.27 (m, 17H), 7.19-7.01 (m, 14H), 3.82-3.63 (m, 7H). $^{13}$C NMR (151 MHz, CDCl$_3$) δ 168.93, 137.56, 137.10, 136.90, 133.57, 130.01, 129.95, 129.26, 128.98, 128.89, 128.75, 127.97, 127.86, 127.85, 127.55, 127.33, 127.08, 126.58, 124.53, 119.84, 119.80, 44.64. HRMS: (ESI) calcd for C$_{22}$H$_{19}$NO [M+H]$^+$ 314.1545; found, 314.1552.

(E)-N-(4-Fluorophenyl)-2-(4-styrylphenyl)acetamide 15f

White powder (72%); mp 223° C. $^1$H NMR (400 MHz, CDCl$_3$) δ 7.60-7.48 (m, 4H), 7.42-7.35 (m, 4H), 7.35-7.31 (m, 2H), 7.29 (d, J=7.4 Hz, 1H), 7.13 (d, J=2.3 Hz, 2H), 7.02 (d, J=7.6 Hz, 1H), 6.97 (dd, J=12.0, 5.4 Hz, 2H), 3.75 (s, 2H). $^{13}$C NMR (151 MHz, CDCl$_3$) δ 168.94, 159.49 (d, J=244.0 Hz), δ 137.02 (d, J=12.4 Hz), 136.97, 133.47 (d, J=14.4 Hz), 129.95, 129.34, 128.77, 127.84 (d, J=14.6 Hz), 127.37, 126.58, 121.72 (d, J=8.2 Hz), 115.63 (d, J=22.8 Hz), 44.46. HRMS: (ESI) calcd for C$_{22}$H$_{18}$FNO [M+H]$^+$ 332.1451; found, 332.1463.

(E)-N-Cyclohexyl-2-(4-styrylphenyl)acetamide 15g

Cream solid (50%); mp. 130° C., $^1$H NMR (600 MHz, CDCl$_3$) δ 7.50 (d, J=6.6 Hz, 1H), 7.36 (d, J=7.3 Hz, 1H), 7.24 (d, J=5.7 Hz, 1H), 7.11 (s, 1H), 3.74 (s, 1H), 3.54 (s, 1H), 2.18 (s, 4H), 1.82 (s, 1H), 1.60 (s, 1H), 1.31 (s, 1H), 1.09 (d, J=11.5 Hz, 1H), 1.01 (d, J=9.7 Hz, 1H ppm. $^{13}$C NMR (151 MHz, CDCl$_3$) δ 169.87, 137.18, 136.41, 134.43, 129.77, 128.93, 128.74, 128.03, 127.76, 127.08, 126.53, 48.23, 43.79, 32.95, 25.46, 24.74 ppm. HRMS calcd for C$_{22}$H$_{25}$NO: 320.1936, found: 320.2024.

General Procedure for the Synthesis of Amides 15h-15i

A mixture of 2-(4-styrylphenyl)acetic acid 6 (2.0 equiv) and excess oxalyl chloride was refluxed at 65° C. for 2 h. After removing oxalyl chloride on rotary evaporator, amines 7h-7i (2.0 equiv) and anhydrous toluene (5.0 mL) were added via syringe and the reaction mixture was stirred overnight. The reaction was monitored by TLC (50% ethyl acetate/hexanes). The reaction was quenched with water (10 mL) and extracted with DCM (3×20 mL). The organic extract was dried over anhydrous sodium sulfate and DCM was removed on rotary evaporator to obtain a brown solid. It was chromatographed on silica gel in 20-50% ethyl acetate/hexanes to yield (E)-2-(4-styrylphenyl)-N-(4-(trifluoromethyl)-phenyl)acetamides 15h-15i.

(E)-2-(4-Stylylphenyl)-N-(4-(trifluoromethyl)phenyl)acetamide 15h

Light brown solid; mp. 235° C., $^1$H NMR (600 MHz, CDCl$_3$) δ 7.60-7.52 (m, 1H), 7.44 (s, 1H), 7.39 (t, J=7.7 Hz, 1H), 7.35 (d, J=8.0 Hz, 1H), 7.19-7.13 (m, 1H), 7.10 (d, J=11.6 Hz, 1H), 3.79 (s, 1H) ppm. $^{13}$C NMR (151 MHz, CDCl$_3$) δ 169.13, 140.58, 137.14, 137.02, 133.01, 129.93, 129.48, 128.78, 127.93, 127.73, 127.44, 126.60, 126.26, 126.24, 119.30, 44.66 ppm. HRMS calcd for C$_{23}$H$_{19}$F$_3$NO: 382.1418, found: 382.1089.

(E)-N-(4-Chlorophenyl)-2-(4-stylylphenyl)acetamide 15i

Light brown solid (44%); mp. 210° C., $^1$H NMR (600 MHz, CDCl$_3$) δ 7.55 (dd, J=17.0, 7.8 Hz, 1H), 7.38 (dd, J=8.1, 5.1 Hz, 1H), 7.34 (d, J=7.9 Hz, 1H), 7.30 (d, J=7.5 Hz, 1H), 7.28-7.23 (m, 4H), 7.14 (d, J=5.8 Hz, 1H), 7.04 (s, 1H), 3.76 (s, 1H), 1.59 (s, 3H) ppm. $^{13}$C NMR (151 MHz, CDCl$_3$) δ 169.04, 159.42, 140.88, 136.99, 136.29, 133.44, 129.93, 129.37, 128.85, 127.85, 127.32, 126.57, 125.15, 124.08, 121.04, 118.65, 110.84, 106.54, 55.92, 44.50, 43.17, 39.97, 36.50, 35.17, 25.42, 15.52 ppm. HRMS calcd for C$_{22}$H$_{18}$ClNO: 348.1076, found: 348.1152.

General Procedure for the Oxidative Cleavage Using OsO$_4$ for the Synthesis of Aldehydes 16a-16i To a solution of 15a-15i (1 equiv) in dioxane:water (2:1) were added 2,6-lutidine (2 equiv), OsO$_4$ (2.5 wt % in 2-methyl-2-propanol, 2 mole %), and NaIO$_4$ (4 equiv). The reaction mixture was stirred at room temperature overnight. Water and dichloromethane were added. The organic layer was separated, and the water layer was extracted with dichloromethane. The combined organic extract was washed with brine and dried over anhydrous sodium sulfate, and the solvent was evaporated under vacuo. The residue was purified by column chromatography on silica gel in ethyl acetate/hexanes (30-50%) to produce 16a-16i.

2-(4-Formylphenyl)-N-(naphthalen-1-yl)acetamide 16a

White powder (95%); mp 296° C. $^1$H NMR (600 MHz, CDCl$_3$) δ 10.09 (s, 1H), 8.01 (d, J=7.9 Hz, 2H), 7.94 (d, J=7.5 Hz, 1H), 7.87 (d, J=7.8 Hz, 1H), 7.72 (d, J=8.2 Hz, 1H), 7.68 (d, J=7.9 Hz, 2H), 7.53-7.40 (m, 5H), 4.01 (s, 2H). $^{13}$C NMR (151 MHz, CDCl$_3$) δ 191.66, 168.26, 141.45, 135.82, 134.06, 131.65, 130.64, 130.33, 128.90, 126.98, 126.52, 126.24, 126.07, 125.71, 120.93, 119.95, 44.83. HRMS: (ESI) calcd for C$_{19}$H$_{15}$NO$_2$ [M+H]$^+$ 290.1181; found, 290.1186.

N-(4-(Dimethylamino)phenyl)-2-(4-formylphenyl)acetamide 16b

The product was used in the next step without further purification.

2-(4-Formylphenyl)-N-(4-methoxyphenyl)acetamide 16c

White powder (99%); mp 193° C. $^1$H NMR (600 MHz, CDCl$_3$) δ 10.05 (s, 1H), 7.93 (d, J=8.1 Hz, 2H), 7.56 (d, J=8.0 Hz, 2H), 7.39-7.33 (m, 2H), 7.03 (s, 1H), 6.88-6.79 (m, 2H), 3.82 (s, 2H), 3.80 (s, 3H). $^{13}$C NMR (151 MHz, CDCl$_3$) δ 191.74, 167.60, 156.74, 141.43, 135.63, 130.42, 130.17, 121.88, 114.17, 55.49, 44.61. HRMS: (ESI) calcd for C$_{16}$H$_{15}$NO$_3$ [M+H]$^+$ 270.1130; found, 270.1141.

2-(4-Formylphenyl)-N-(p-tolyl)acetamide 16d

White crystals (55%); mp. 120° C., $^1$H NMR (600 MHz, CDCl$_3$) δ 10.02 (s, 1H), 7.88 (d, J=8.1 Hz, 2H), 7.46 (d, J=8.0 Hz, 2H), 3.62 (s, 3H), 1.87 (d, J=8.9 Hz, 3H), 1.65 (d, J=13.6 Hz, 8H), 1.59 (d, J=13.2 Hz, 3H), 1.34 (d, J=13.4 Hz, 3H), 1.12 (d, J=12.6 Hz, 1H), 1.05 (d, J=11.1 Hz, 2H) ppm. $^{13}$C NMR (151 MHz, CDCl$_3$) δ 191.73, 167.57, 141.37, 135.64, 134.80, 134.48, 130.42, 130.17, 129.54, 119.97, 44.76, 20.88 ppm.

2-(4-Formylphenyl)-N-phenylacetamide 16e

White powder (93%); mp 183-185° C. $^1$H NMR (400 MHz, CDCl$_3$) δ 10.03 (s, 1H), 7.91 (d, J=8.0 Hz, 2H), 7.54 (d, J=8.0 Hz, 2H), 7.44 (d, J=8.0 Hz, 2H), 7.30 (t, J=7.9 Hz, 2H), 7.11 (t, J=7.4 Hz, 2H), 3.82 (s, 2H). $^{13}$C NMR (151 MHz, CDCl$_3$) δ 191.74, 167.72, 141.25, 137.37, 135.66, 130.44, 130.17, 129.07, 124.78, 119.87, 44.79. HRMS: (ESI) calcd for C$_{15}$H$_{13}$NO$_2$ [M+H]$^+$ 240.1025; found, 240.1031.

N-(4-Fluorophenyl)-2-(4-formylphenyl)acetamide 16f

Yellow powder (99%); mp 183-184° C. $^1$H NMR (600 MHz, CDCl$_3$) δ 10.05 (s, 1H), 7.93 (d, J=8.1 Hz, 2H), 7.53 (dd, J=16.6, 6.4 Hz, 2H), 7.47-7.38 (m, 2H), 7.17 (s, 1H), 7.06-6.98 (m, 2H), 3.83 (s, 2H). $^{13}$C NMR (151 MHz, CDCl$_3$) δ 191.74, 167.77, 159.59 (d, J=244.1 Hz), 141.14, 135.68, 133.35, 133.34, 130.31 (d, J=44.0 Hz), 121.82 (d, J=8.0 Hz), 115.74 (d, J=22.4 Hz), 77.25, 77.04, 76.83, 44.59. HRMS: (ESI) calcd for C$_{15}$H$_{12}$FNO$_2$ [M+H]$^+$ 258.0930; found, 258.0934.

N-Cyclohexyl-2-(4-formylphenyl)acetamide 16g

White solid (40%); mp. 160° C., $^1$H NMR (600 MHz, CDCl$_3$) δ 10.02 (s, 1H), 8.07 (d, J=8.2 Hz, 1H), 7.88 (d, J=8.1 Hz, 2H), 7.46 (d, J=8.0 Hz, 2H), 7.38 (d, J=8.1 Hz, 1H), 5.24 (s, 1H), 3.78 (s, 1H), 3.62 (s, 2H), 1.87 (d, J=12.4 Hz, 3H), 1.71-1.62 (m, 7H), 1.60 (dd, J=13.0, 3.7 Hz, 3H), 1.37 (d, J=3.4 Hz, 1H), 1.34 (d, J=13.4 Hz, 2H), 1.31 (s, 1H), 1.15 (s, 1H), 1.12 (d, J=12.6 Hz, 1H), 1.08 (s, 1H), 1.05 (d, J=11.1 Hz, 2H), 1.03 (s, 1H) ppm. $^{13}$C NMR (151 MHz, CDCl$_3$) δ 191.82, 142.15, 130.76, 130.28, 129.97, 129.49, 77.24, 77.03, 76.82, 48.49, 44.06, 32.99, 25.43, 24.74 ppm. HRMS calcd for C$_{15}$H$_{15}$NO$_2$: 246.1415, found: 246.1497.

2-(4-Formylphenyl)-N-(4-(trifluoromethyl)phenyl)acetamide 16h

Cream solid (46%); mp. 170° C., $^1$H NMR (400 MHz, CDCl$_3$) δ 10.05 (s, 1H), 7.94 (d, J=8.1 Hz, 2H), 7.56 (dd, J=15.5, 5.2 Hz, 6H), 3.86 (s, 2H), 1.56 (s, 2H) ppm. $^{13}$C NMR (151 MHz, CDCl$_3$) δ 191.62, 140.64, 130.51, 130.17, 126.37, 126.34, 119.39, 44.79 ppm. HRMS calcd for C$_{16}$H$_{13}$F$_3$NO$_2$: 308.0898, found: 308.0907.

N-(4-Chlorophenyl)-2-(4-formylphenyl)acetamide 16i

Cream solid (76%); mp. 195° C. $^1$H NMR (600 MHz, CDCl$_3$) δ 10.01 (s, 1H), 7.90 (d, J=8.0 Hz, 1H), 7.50 (d, J=8.0 Hz, 1H), 7.38 (d, J=8.8 Hz, 1H), 7.02 (s, 1H), 3.79 (s, 1H), 1.53 (s, 1H) ppm. $^{13}$C NMR (151 MHz, CDCl$_3$) δ 191.67, 167.71, 140.94, 135.93, 135.74, 130.47, 130.16, 129.78, 129.09, 121.10, 44.71 ppm.

General Procedure for the Aldol Reaction Using Piperidine for the Synthesis of Compounds 17-26

To a mixture of 19a-19i (1 equiv) and 2 (1.2 equiv) in methanol in a microwave vial was added piperidine (4 equiv). The reaction mixture was heated in a microwave synthesizer for 4 h at 90° C. The solvent was removed under reduced pressure, and the residue was purified by column chromatography on silica gel in ethyl acetate/hexanes to give 17-26 (50-75%).

(E)-2-(4-(3-(1H-imidazol-2-yl)-3-oxoprop-1-en-1-yl)phenyl)-N-(naphthalen-1-yl)acetamide 17

Yellow powder (55%); mp 229-230° C. $^1$H NMR (600 MHz, DMSO-d6) δ 10.22 (s, 2H), 8.06 (d, J=8.0 Hz, 3H), 8.00-7.91 (m, 6H), 7.86 (dd, J=13.8, 9.1 Hz, 3H), 7.81 (s, J=8.0 Hz, 4H), 7.78 (d, J=8.1 Hz, 2H), 7.67 (t, J=10.9 Hz, 3H), 7.60-7.46 (m, 15H), 7.28 (s, 2H), 3.89 (s, 4H). $^{13}$C NMR (151 MHz, DMSO-d6) δ 178.94, 169.89, 146.29, 143.26, 139.69, 134.16, 133.82, 133.33, 130.42, 129.21, 128.65, 128.18, 126.53, 126.38, 126.03, 125.85, 123.02, 122.23, 121.92, 43.20. HRMS: (ESI) calcd for C$_{24}$H$_{19}$N$_3$O$_2$ [M+H]$^+$ 382.1556; found, 382.1568.

(E)-2-(4-(3-(1H-imidazol-2-yl)-3-oxoprop-1-en-1-yl)phenyl)-N-(4-(dimethylamino)phenyl)acetamid 18

Yellow powder (30%); mp 221° C. $^1$H NMR (600 MHz, CD$_3$OD) δ 7.92 (q, J=15.9 Hz, 1H), 7.74 (dd, J=20.6, 5.3 Hz, 1H), 7.48 (d, J=8.1 Hz, 1H), 7.43-7.34 (m, 2H), 6.80 (d, J=9.0 Hz, 1H), 3.73 (s, 2H), 2.92 (s, 3H). $^{13}$C NMR (151 MHz, CD$_3$OD) δ 178.62, 169.86, 145.96, 143.87, 138.96, 133.43, 129.53, 128.61, 121.56, 120.59, 113.27, 42.99, 40.11. HRMS: (ESI) calcd for C$_{22}$H$_{22}$N$_4$O$_2$ [M+H]$^+$ 375.1821; found, 375.1811.

(E)-2-(4-(3-(1H-imidazol-2-yl)-3-oxoprop-1-en-1-yl)phenyl)-N-(4-methoxyphenyl)acetamide 19

White powder (30%); mp 224-226° C. $^1$H NMR (400 MHz, CD$_3$OD) δ 7.97-7.82 (m, 2H), 7.73 (d, J=8.2 Hz, 2H), 7.44 (dt, J=5.4, 4.7 Hz, 5H), 7.29 (s, 1H), 6.91-6.81 (m, 2H), 3.76 (s, 3H), 3.71 (s, 2H). $^{13}$C NMR (151 MHz, CD$_3$OD) δ 178.63, 169.99, 156.62, 143.85, 138.83, 133.46, 131.33, 129.55, 128.62, 121.69, 120.60, 113.54, 54.42, 42.99. HRMS: (ESI) calcd for C$_{21}$H$_{19}$N$_3$O$_3$ [M+H]$^+$ 362.1505; found, 362.1515.

(E)-2-(4-(3-(1H-Imidazol-2-yl)-3-oxoprop-1-en-1-yl)phenyl)-N-(p-tolyl)acetamide 20

Cream solid (22%); mp. 218.5° C., $^1$H NMR (600 MHz, CD$_3$OD) δ 7.86 (q, J=15.9 Hz, 1H), 7.69 (d, J=8.1 Hz, 1H), 7.42 (d, J=8.1 Hz, 1H), 7.38 (d, J=8.4 Hz, 1H), 7.07 (d, J=8.2 Hz, 1H), 3.26 (s, 9H), 2.25 (s, 2H) ppm. $^{13}$C NMR (151 MHz, CD$_3$OD) δ 178.62, 170.08, 145.98, 143.91, 143.81, 143.74, 138.77, 135.81, 133.70, 133.47, 129.67, 129.45, 128.94, 128.79, 128.70, 128.51, 120.70, 120.63, 120.53, 120.08, 120.03, 119.86, 48.02, 47.88, 47.73, 47.59, 47.45, 47.31, 47.17, 43.09, 19.51, 19.47 ppm. HRMS calcd for C$_{21}$H$_{20}$N$_3$O$_2$: 346.1555, found: 346.1573.

(E)-2-(4-(3-(1H-Imidazol-2-yl)-3-oxoprop-1-en-1-yl)phenyl)-N-phenylacetamide 21

Off-white powder (45%); mp 211-214° C. $^1$H NMR (600 MHz, acetone-d$_6$) δ 9.40 (s, 1H), 8.00-7.92 (m, 1H), 7.89-7.81 (m, 1H), 7.74 (d, J=8.0 Hz, 2H), 7.64 (d, J=7.9 Hz, 2H), 7.47 (d, J=9.4 Hz, 3H), 7.26 (t, J=7.8 Hz, 3H), 7.02 (t, J=7.3 Hz, 1H), 3.75 (s, 2H). $^{13}$C NMR (151 MHz, acetone-d$_6$) δ 178.60, 168.43, 168.34, 146.29, 142.79, 139.47, 139.38, 138.89, 133.52, 130.99, 130.92, 129.98, 129.10, 128.65, 128.62, 126.95, 123.34, 121.53, 121.30, 119.19, 119.10, 43.68, 43.64. HRMS: (ESI) calcd for C$_{20}$H$_{17}$N$_3$O$_2$ [M+H]$^+$ 332.1399; found, 332.1401.

(E)-2-(4-(3-(1H-Imidazol-2-yl)-3-oxoprop-1-en-1-yl)phenyl)-N-(4-fluorophenyl)acetamide 22

White powder (30%); mp 224-226° C. $^1$H NMR (400 MHz, CD$_3$OD) δ 7.95-7.83 (m, 2H), 7.72 (d, J=8.2 Hz, 2H), 7.58-7.53 (m, 2H), 7.45 (d, J=8.2 Hz, 2H), 7.29 (s, 1H), 7.07-7.00 (m, 2H), 3.72 (s, 2H). $^{13}$C NMR (151 MHz, CD$_3$OD) δ 178.62, 170.16, 159.33 (d, J=242.0 Hz), 145.96, 143.80, 138.59, 134.63, 133.51, 129.57, 128.62, 121.73 (d, J=7.7 Hz), 120.64, 114.88 (d, J=22.6 Hz), 43.00. HRMS: (ESI) calcd for C$_{20}$H$_{16}$FN$_3$O$_2$ [M+H]$^+$ 350.1305; found, 350.1310.

(E)-2-(4-(3-(1H-Imidazol-2-yl)-3-oxoprop-1-en-1-yl)phenyl)-N-cyclohexylacetamide 23

Cream solid (25%); mp. 208.5° C., $^1$H NMR (600 MHz, CDCl$_3$) δ 11.86 (t, J=11.0 Hz, 1H), 11.66 (d, J=8.2 Hz, 1H), 11.39-11.31 (m, 2H), 7.27 (dt, J=3.3, 1.6 Hz, 3H), 5.81 (d, J=9.6 Hz, 1H), 5.71 (dd, J=10.3, 3.2 Hz, 1H), 5.59 (d, J=12.8 Hz, 1H), 5.37-5.12 (m, 4H) ppm. $^{13}$C NMR (151 MHz, CDCl$_3$) δ 179.30, 169.31, 146.19, 144.25, 138.09, 133.76, 129.95, 129.42, 121.21, 77.25, 77.04, 76.82, 48.37, 43.91, 32.95, 29.72, 25.44, 24.72 ppm. HRMS calcd for C$_{20}$H$_{24}$N$_3$O$_2$: 338.1868, found: 338.1881.

(E)-2-(4-(3-(1H-Imidazole-2-yl)-3-oxoprop-1-en-1-yl)phenyl)-N-(4-(trifluoromethyl)phenyl)acetamide 24

Cream solid (30%); mp. 240.5° C., $^1$H NMR (600 MHz, CD$_3$OD) δ 7.90 (q, J=15.9 Hz, 2H), 7.78 (d, J=8.6 Hz, 3H), 7.74 (d, J=8.2 Hz, 3H), 7.60 (d, J=8.7 Hz, 3H), 7.46 (d, J=8.1 Hz, 3H), 7.42 (s, 1H), 7.29 (s, 1H), 5.50 (s, 1H), 3.78 (s, 3H), 2.01 (s, 1H) ppm. $^{13}$C NMR (151 MHz, CD$_3$OD) δ 178.62, 178.60, 170.52, 170.50, 145.97, 143.76, 142.06, 138.29, 133.58, 130.14, 129.63, 128.62, 125.66, 125.63, 125.16, 120.70, 119.37, 43.14 ppm. HRMS calcd for C$_{21}$H$_{17}$F$_3$N$_3$O$_2$: 400.1273, found: 413.2071.

(E)-2-(-4(3-(1H-imidazol-2-yl)-3-oxoprop-1-en-1-yl)phenyl)-N-(4-chlorophenyl)acetamide 25

Cream solid (51%); mp. 244° C., $^1$H NMR (600 MHz, CD$_3$OD) δ 7.92-7.84 (m, 1H), 7.72 (d, J=8.2 Hz, 1H), 7.57-7.54 (m, 1H), 7.44 (d, J=8.2 Hz, 1H), 7.35 (s, 1H), 7.29-7.26 (m, 1H), 3.71 (d, J=10.5 Hz, 1H), 3.35-3.32 (m, 1H), 1.32-1.25 (m, 2H) ppm. $^{13}$C NMR (151 MHz, CD$_3$OD) δ 143.78, 138.49, 129.59, 128.72, 128.61, 128.40, 121.13, 120.67, 43.08 ppm. HRMS calcd for C$_{20}$H$_{17}$ClN$_3$O$_2$: 366.1009, found: 366.1037.

(E)-2-(4-(3-(1-Methyl-1H-imidazol-2-yl)-3-oxoprop-1-en-1-yl)phenyl)-N-(4-(trifluoromethyl)phenyl)acetamide 26

White solid (26%); mp. 222-226° C. $^1$H NMR (600 MHz, CDCl$_3$) δ 8.10 (d, J=16.0 Hz, 1H), 7.83 (d, J=16.0 Hz, 1H), 7.74 (d, J=8.0 Hz, 2H), 7.57 (q, J=8.8 Hz, 5H), 7.39 (d, J=8.0 Hz, 2H), 7.24 (d, J=5.1 Hz, 2H), 7.11 (s, 1H), 4.12 (s, 3H), 3.80 (s, 2H). $^{13}$C NMR (151 MHz, CDCl$_3$) δ 180.33, 168.64, 143.98, 142.37, 140.52, 136.16, 134.65, 130.04, 129.58, 129.43, 127.46, 126.28 (d, J=3.4 Hz), 126.27, 123.36, 119.36, 44.72, 36.44.

General Procedure for the N1-Alkylation Using Alkyl Iodide for the Synthesis of Amides 27-31

To a stirred solution of 21-25 (1 equiv) in dimethylformamide (0.5 mL) were added alkyl iodide (1.2 equiv), and sodium carbonate (2 equiv). The reaction mixture was stirred overnight at room temperature. Water and dichloromethane were added. The organic layer was separated, and the water layer was extracted with dichloromethane. The combined organic extract was washed with brine, dried over anhydrous sodium sulfate, and the solvent was evaporated under vacuo. The residue was purified by column chromatography on silica gel in ethyl acetate/hexanes to produce 27-31 (35-55%).

(E)-2-(4-(3-(1-Methyl-1H-imidazol-2-yl)-3-oxoprop-1-en-1-yl)phenyl)-N-phenylacetamide 27

White powder (60%); mp 184-186° C. $^1$H NMR (400 MHz, acetone-d$_6$) δ 9.40 (s, 1H), 8.11 (d, J=16.1 Hz, 1H), 7.81-7.68 (m, 3H), 7.66 (d, J=8.2 Hz, 2H), 7.49 (d, J=8.1 Hz, 2H), 7.39 (d, J=8.5 Hz, 1H), 7.28 (t, J=7.9 Hz, 2H), 7.16 (s, 1H), 7.04 (t, J=7.4 Hz, 1H), 4.08 (s, 3H), 3.77 (s, 2H). $^{13}$C NMR (151 MHz, acetone-d$_6$) δ 179.74, 168.44, 143.95, 141.85, 139.47, 138.68, 133.63, 129.95, 128.97, 128.64, 128.52, 127.90, 123.34, 122.84, 119.19, 43.68, 35.45. HRMS: (ESI) calcd for C$_{21}$H$_{19}$N$_3$O$_2$ [M+H]$^+$ 346.1556; found, 346.1554.

(E)-N-(4-Fluorophenyl)-2-(4-(3-(1-methyl-1H-imidazol-2-yl)-3-oxoprop-1-en-1-yl)phenyl)acetamide 28

White powder (33%); mp 213° C. $^1$H NMR (600 MHz, acetone-d$_6$) δ 9.45 (s, 1H), 8.12 (d, J=16.1 Hz, 1H), 7.77 (dd, J=16.4, 12.1 Hz, 3H), 7.72-7.65 (m, 2H), 7.50 (d, J=8.1 Hz, 2H), 7.42 (s, 1H), 7.18 (d, J=0.8 Hz, 1H), 7.11-7.04 (m, 2H), 4.10 (s, 3H), 3.77 (s, 2H). $^{13}$C NMR (151 MHz, acetone-d$_6$) δ 179.73, 168.37, 158.70 (d, J=240.5 Hz), 143.96, 141.80, 138.55, 135.76, 133.66, 129.95, 128.98, 128.52, 127.90, 122.87, 120.96 (d, J=7.7 Hz), 115.06 (d, J=22.8 Hz), 43.55, 35.44. HRMS: (ESI) calcd for C$_{21}$H$_{18}$FN$_3$O$_2$ [M+H]$^+$ 364.1461; found, 364.1468.

(E)-N-Cyclohexyl-2-(4-(3-(1-methyl-1-H-imidazol-2-yl)-3-oxoprop-1-en-1-yl) phenyl) acetamide 29

White crystals (38%); mp. 182.5° C. $^1$H NMR (600 MHz, CD$_3$OD) δ 8.13 (d, J=6.7 Hz, 1H), 7.98 (d, J=15.9 Hz, 1H), 7.79 (d, J=15.9 Hz, 1H), 7.69 (d, J=8.1 Hz, 2H), 7.49 (s, 1H), 7.42-7.35 (m, 3H), 7.21 (s, 1H), 7.09 (s, 1H), 4.09 (s, 3H), 3.69-3.58 (m, 1H), 3.52 (s, 2H), 1.91-1.59 (m, 7H), 1.42-1.28 (m, 3H), 1.27-1.14 (m, 4H) ppm. $^{13}$C NMR (151 MHz, CD$_3$OD) δ 179.85, 171.01, 143.20, 138.98, 133.43, 129.33, 128.47, 127.91, 121.87, 48.54, 42.34, 35.33, 32.32, 25.22, 24.71 ppm. HRMS calcd for C$_{21}$H$_{26}$N$_3$O$_2$: 352.2025, found: 352.2038.

(E)-N-(4-chlorophenyl)-2-(4-(3-(1-methyl-1H-imidazol-2-yl)-3-oxoprop-1-en-1-yl) phenyl)acetamide 30

Cream solid (12%); mp. 250° C. $^1$H NMR (600 MHz, CD$_3$OD) δ 8.01-7.78 (m, 1H), 7.72 (d, J=8.1 Hz, 1H), 7.59-7.55 (m, 1H), 7.44 (d, J=8.1 Hz, 1H), 7.40 (s, 1H), 7.31-7.28 (m, 1H), 7.20 (s, 1H), 4.08 (s, 1H), 3.72 (d, J=9.6 Hz, 1H) ppm. $^{13}$C NMR (151 MHz, CD$_3$OD) δ 179.83, 170.25, 143.13, 143.05, 138.29, 137.31, 133.62, 129.55, 128.71, 128.55, 128.40, 128.35, 127.93, 121.99, 121.12, 43.07, 35.33 ppm. HRMS calcd for C$_{21}$H$_{19}$ClN$_3$O$_2$: 380.1165, found: 380.1170.

(E)-2-(4-(3-(1-Ethyl-1H-imidazol-2-yl)-3-oxoprop-1-en-1-yl)phenyl)-N-(4-fluorophenyl)acetamide 31

White powder (63%); mp 219-220° C. $^1$H NMR (400 MHz, CDCl$_3$) δ 8.11 (d, J=16.0 Hz, 1H), 7.80 (d, J=16.0 Hz, 1H), 7.72 (d, J=8.0 Hz, 2H), 7.43-7.34 (m, 4H), 7.24 (s, 1H), 7.17 (s, 1H), 7.07 (s, 1H), 6.98 (t, J=8.6 Hz, 2H), 4.55 (q, J=7.2 Hz, 2H), 3.76 (s, 2H), 1.48 (t, J=7.2 Hz, 3H). $^{13}$C NMR (151 MHz, CDCl$_3$) δ 180.11, 168.39, 159.53 (d, J=244.2 Hz), 143.40, 142.29, 136.53, 134.56, 133.45, 130.04, 129.64, 129.52, 125.73, 123.50, 121.76 (d, J=8.1 Hz), 115.66 (d, J=22.6 Hz), 44.56, 44.06, 29.72, 16.55. HRMS: (ESI) calcd for C$_{22}$H$_{20}$FN$_3$O$_2$ [M+H]$^+$ 379.1618; found, 379.1618.

2-(4-(3-1H-imidazol-2-yl)-3-oxopropyl)phenyl)-N-phenylacetamide 32

A mixture of (E)-2-(4-(3-(1H-imidazol-2-yl)-3-oxoprop-1-en-1-yl)phenyl)-N-phenylacetamide 21 (7 mg, 0.021 mmol, 1 equiv) and 5% Pd/C (10 wt. %) in MeOH (1 mL) was stirred under hydrogen at 3 atm for 5 h. After disappearance of starting material (TLC), the reaction mixture was filtered through a pad of celite, concentrated in vacuo, and the residue was purified by column chromatography on silica gel in ethyl acetate/hexanes (30-50%) to give 32 as a white powder (5.5 mg, 79%); mp 193-195° C. $^1$H NMR (400 MHz, acetone-d$_6$) δ 9.28 (s, 1H), 7.64 (d, J=7.6 Hz, 2H), 7.40 (s, 1H), 7.26 (dt, J=17.9, 6.5 Hz, 6H), 7.18 (s, 1H), 7.03 (t, J=7.4 Hz, 1H), 3.64 (s, 2H), 3.36 (dd, J=9.4, 5.9 Hz, 2H), 3.00 (t, J=7.6 Hz, 2H). $^{13}$C NMR (151 MHz, acetone-d$_6$) δ 190.04, 168.99, 145.34, 139.86, 139.56, 133.59, 130.60, 129.27, 129.16, 128.60, 128.39, 126.76, 123.21, 120.89, 120.74, 119.11, 43.51, 39.02. HRMS: (ESI) calcd for C$_{20}$H$_{19}$N$_3$O$_2$ [M+H]$^+$ 334.1555; found, 334.1559.

(E)-2-(4-(3-(1H-imidazol-2-yl)-3-oxoprop-1-en-1-yl) phenyl)-N-(3,4,5-trifluorophenyl) acetamide 33

To a mixture of 1-(1H-imidazol-2-yl) ethan-1-one 5 (29 mg, 0.263 mmol) and 2-(4-formylphenyl)-N-(3,4,5-trifluorophenyl) acetamide (100 mg, 0.342 mmol, 1.3 eq) in a microwave vial under nitrogen were added piperidine (65 µL, 0.658 mmol, 2.5 eq) and anhydrous methanol (5.0 mL) via syringe. The reaction mixture was heated in the microwave synthesizer for 5 h and it was monitored by TLC (50% ethyl acetate/hexanes). Methanol was removed on a rotary evaporator to obtain a brown oil. It was chromatographed on silica gel in 50-75% ethyl acetate/hexanes to obtain (E)-2-(4-(3-(1H-imidazol-2-yl)-3-oxoprop-1-en-1-yl) phenyl)-N-(3,4,5-trifluorophenyl) acetamide 33 as a brown solid (22 mg, 21.7%). TLC R$_f$=0.1 (50% ethyl acetate/hexanes), mp 255° C. $^1$H NMR (600 MHz, CD$_3$OD) δ 7.89, 7.87, 7.84, 7.81, 7.69 (d, J=8.0 Hz, 5H), 7.38 (dd, J=16.4, 9.0 Hz, 13H), 7.25 3.69. $^{13}$C NMR (151 MHz, MeOD) δ 178.60, 170.35, 151.67 (d, J=5.1 Hz), 151.60 (d, J=5.0 Hz), 145.97, 143.72, 138.06, 133.63, 130.14, 129.61, 128.62, 121.40, 120.75, 103.65 (dd, J=20.5, 5.4 Hz), 43.06 ppm. HRMS calcd for C$_{20}$H$_{16}$F$_3$N$_3$O$_2$: 387.12, found: 387.1138.

(E)-2-(4-(3-(1-methyl-1H-imidazol-2-yl)-3-oxoprop-1-en-1-yl) phenyl)-N-(3,4,5-trifluorophenyl)acetamide 34

To a mixture of 1-(1-methyl-1H-imidazol-2-yl) ethan-1-one (65 mg, 0.524 mmol) and 2-(4-formylphenyl)-N-(3,4,5-trifluorophenyl) acetamide (199.6 mg, 0.681 mmol, 1.3 eq) in a microwave vial under nitrogen were added piperidine (129 µL, 1.3 mmol, 2.5 eq) and anhydrous methanol (5.0 mL) via syringe. The reaction mixture was heated in the microwave synthesizer for 5 h and it was monitored by TLC (50% ethyl acetate/hexanes). Methanol was remove on a rotary evaporator to obtain a brown oil. It was chromatographed on silica gel in 50-75% ethyl acetate/hexanes to obtain (E)-2-(4-(3-(1-methyl-1H-imidazol-2-yl)-3-oxoprop-1-en-1-yl) phenyl)-N-(3,4,5-trifluorophenyl) acetamide 34 as a brown solid (49 mg, 23.4%). TLC R$_f$=0.1 (50% ethyl acetate/hexanes), mp 222° C. $^1$H NMR (600 MHz, CDCl$_3$) δ δ 8.11 (s, 1H), 8.08 (s, 1H), 7.83 (s, 1H), 7.80 (s, 1H), 7.72 (d, J=8.1 Hz, 34H), 7.36 (d, J=8.1 Hz, 2H), 7.25 (s, 1H), 7.20 (s, 10H), 7.19 (d, J=3.0 Hz, 1H), 7.18 (s, 1H), 7.12 (s, 1H), 4.12 (s, 3H), 3.77 (s, 2H). $^{13}$C NMR (151 MHz, CDCl$_3$) δ 180.18, 168.56, 151.90 (dd, J=10.3, 5.2 Hz), 150.25 (dd, J=10.3, 5.3 Hz), 142.40, 135.94, 134.69, 133.09, 129.99, 129.62, 127.46, 123.38, 104.19 (dd, J=20.1, 6.0 Hz), 44.55, 36.48 ppm. HRMS calcd for C$_{21}$H$_{18}$F$_3$N$_3$O$_2$: 401.14, found: 401.1356.

(E)-2-(4-(3-(1H-imidazol-2-yl)-3-oxoprop-1-en-1-yl) phenyl)-N-(perfluorophenyl)acetamide 35

To a mixture of 1-(1H-imidazol-2-yl) ethan-1-one (32 mg, 0.290 mmol) and 2-(4-formylphenyl)-N-(perfluorophenyl) acetamide (124 mg, 0.377 mmol, 1.3 eq) in a microwave vial under nitrogen were added piperidine (61 µL, 0.726 mmol, 2.5 eq) and anhydrous methanol (5.0 mL) via syringe. The reaction mixture was heated in the microwave synthesizer for 5 h and it was monitored by TLC (50% ethyl acetate/hexanes). Methanol was removed on a rotary evaporator to obtain a brown oil. It was chromatographed by preparative TLC in 50-75% ethyl acetate/hexanes to obtain (E)-2-(4-(3-(1H-imidazol-2-yl)-3-oxoprop-1-en-1-yl) phenyl)-N-(perfluorophenyl) acetamide 35 as a brown solid (16 mg, 13.07%). TLC R$_f$=0.5 (50% ethyl acetate/hexanes), mp 235° C. $^1$H NMR (600 MHz, CD$_3$OD) δ 7.94 (s, 1H), 7.92 (s, 2H), 7.89 (s, 2H), 7.86 (s, 1H), 7.75 (d, J=8.1 Hz, 6H), 7.46 (d, J=8.0 Hz, 6H), 7.41 (s, 3H), 7.29 (s, 3H), 3.83 (s, 7H). $^{13}$C NMR (151 MHz, MeOD) δ 178.61, 170.86, 166.79, 145.98, 140.81, 137.75, 133.73, 130.15, 129.59, 128.66, 121.42, 120.82, 41.70 ppm. HRMS calcd for C$_{20}$H$_{14}$F$_5$N$_3$O$_2$: 423.10 found: 423.1146.

(E)-2-(4-(3-(1-methyl-1H-imidazol-2-yl)-3-oxoprop-1-en-1-yl) phenyl)-N-(perfluorophenyl)acetamide 36

To a mixture of 1-(1-methyl-1H-imidazol-2-yl) ethan-1-one (65 mg, 0.524 mmol) and 2-(4-formylphenyl)-N-(perfluorophenyl)acetamide (224.09 mg, 0.681 mmol, 1.3 eq) in a microwave vial under nitrogen were added piperidine (129 µL, 1.3 mmol, 2.5 eq) and anhydrous methanol (5.0 mL) via syringe. The reaction mixture was heated in the microwave synthesizer for 5 h and it was monitored by TLC (50% ethyl acetate/hexanes). Methanol was removed on a rotary evaporator to obtain a brown oil. It was chromatographed on silica gel in 50-75% ethyl acetate/hexanes to obtain (E)-2-(4-(3-(1-methyl-1H-imidazol-2-yl)-3-oxoprop-1-en-1-yl) phenyl)-N-(perfluorophenyl)acetamide 36 as a brown solid (30 mg, 13.1%). TLC $R_f$=0.7 (50% ethyl acetate/hexanes), mp 248° C. $^1$H NMR (600 MHz, CDCl$_3$) δ 8.08 (s, 1H), 8.06 (s, 1H), 7.81 (s, 1H), 7.79 (s, 1H), 7.72 (d, J=8.1 Hz, 4H), 7.40 (d, J=7.8 Hz, 4H), 7.24 (s, 2H), 7.11 (s, 2H), 6.87 (s, 2H), 4.11 (s, 7H), 3.86 (s, 5H). $^{13}$C NMR (151 MHz, CDCl$_3$) δ 180.27, 168.85, 143.94, 142.33, 135.90, 134.68, 129.95, 129.58, 129.40, 127.47, 123.32, 123.32, 43.28, 36.45 ppm. HRMS calcd for $C_{21}H_{16}F_5N_3O_2$: 437.12, found: 437.1146.

(E)-2-(4-(3-(1H-imidazol-2-yl)-3-oxoprop-1-en-1-yl) phenyl)-N-(3,5-bis(trifluoromethyl)phenyl) acetamide 37

To a mixture of 1-(1H-imidazol-2-yl) ethan-1-one (32 mg, 0.272 mmol) and N-(3,5-bis(trifluoromethyl)phenyl)-2-(4-formylphenyl) acetamide (133 mg, 0.354 mmol, 1.3 eq) in a microwave vial under nitrogen were added piperidine (67 µL, 0.681 mmol, 2.5 eq) and anhydrous methanol (5.0 mL) via syringe. The reaction mixture was heated in the microwave synthesizer for 5 h and it was monitored by TLC (50% ethyl acetate/hexanes). Methanol was removed on a rotary evaporator to obtain a brown oil. It was chromatographed on silica gel in 50-75% ethyl acetate/hexanes to obtain (E)-2-(4-(3-(1H-imidazol-2-yl)-3-oxoprop-1-en-1-yl) phenyl)-N-(3,5-bis(trifluoromethyl)phenyl) acetamide 37 as a white solid (35 mg, 27.5%). TLC $R_f$=0.6 (50% ethyl acetate/hexanes), mp 243° C.$^1$H NMR (600 MHz, CD$_3$OD) δ 8.19 (s, 1H), 7.90 (s, 1H), 7.87 (s, 1H), 7.85 (s, 1H), 7.82 (s, 1H), 7.71 (d, J=8.2 Hz, 1H), 7.61 (s, 1H), 7.43 (d, J=8.1 Hz, 1H), 7.38 (s, 1H), 7.25 (s, 1H), 3.76 (s, 1H). $^{13}$C NMR (151 MHz, MeOD) δ 178.61, 170.74, 145.97, 143.73, 140.68, 137.89, 133.68, 132.19, 131.97, 131.75, 131.53, 130.56, 130.14, 129.67, 128.65, 120.77, 43.10 ppm. HRMS calcd for $C_{22}H_{17}F_6N_3O_2$: 469.12 found: 469.1202.

(E)-N-(3,5-Bis(trifluoromethyl)phenyl)-2-(4-(3-(1-methyl-1H-imidazol-2-yl)-3-oxoprop-1-en-1-yl) phenyl) acetamide 38

To a mixture of 1-(1-methyl-1H-imidazol-2-yl) ethan-1-one (30 mg, 0.241 mmol) and N-(3,5-bis(trifluoromethyl)phenyl)-2-(4-formylphenyl) acetamide (117.89 mg, 0.314 mmol, 1.3 eq) in a microwave vial under nitrogen were added piperidine (60 µL, 0.604 mmol, 2.5 eq) and anhydrous methanol (5.0 mL) via syringe. The reaction mixture was heated in the microwave synthesizer for 5 h and it was monitored by TLC (50% ethyl acetate/hexanes). Methanol was remove on a rotary evaporator to obtain a brown oil. It was chromatographed on silica gel in 50-75% ethyl acetate/hexanes to obtain (E)-N-(3,5-bis(trifluoromethyl)phenyl)-2-(4-(3-(1-methyl-1H-imidazol-2-yl)-3-oxoprop-1-en-1-yl) phenyl) acetamide 38 as a brown solid (30 mg, 30%). TLC $R_f$=0.7 (50% ethyl acetate/hexanes), mp 215° C. $^1$H NMR (600 MHz, CDCl$_3$) δ 8.13 (s, 1H), 8.10 (s, 1H), 7.99 (s, 2H), 7.84 (s, 1H), 7.81 (s, 1H), 7.74 (d, J=8.1 Hz, 2H), 7.59 (s, 1H), 7.38 (d, J=8.0 Hz, 1H), 7.13 (s, 1H), 4.13 (s, 2H), 3.82 (s, 1H). $^{13}$C NMR (151 MHz, CDCl$_3$) δ 180.06, 168.89, 143.71, 142.59, 138.99, 135.85, 134.69, 132.68, 132.46, 132.24, 132.02, 130.02, 129.67, 127.44, 123.33, 119.49, 44.55, 36.52 ppm. HRMS calcd for $C_{23}H_{19}F_6N_3O_2$: 483.14 found: 483.1382.

(E)-2-(4-(3-(1-methyl-1H-imidazol-2-yl)-3-oxoprop-1-en-1-yl)phenyl)-N-(4-(5-methylbenzo[d]thiazol-2-yl)phenyl)acetamide 39

A mixture of (E)-2-(4-(3-(1-methyl-1H-imidazol-2-yl)-3-oxoprop-1-en-1-yl)phenyl)acetic acid 46 (100 mg, 0.37 mmol), anhydrous DCM (4 mL), EDC (134 mg, 0.7 mmol, 1.9 equivalent) and a catalytic amount of DMAP (10 mol %) was stirred for 5 min. Then 4-(5-methylbenzo[d]thiazol-2-yl)aniline (96 mg, 0.4 mmol, 1.1 equivalent) was added and the reaction mixture was stirred at room temperature overnight. The solvent was removed under reduced pressure and the crude mixture was separated by flash chromatography on silica gel in ethyl acetate: hexanes (20%→50% ethyl acetate) to obtain the pure product 39 (58 mg, 32%). $^1$H NMR (600 MHz, CDCl$_3$) δ 8.10 (d, J=16.0 Hz, 1H), 7.97 (d, J=8.6 Hz, 2H), 7.88 (d, J=8.4 Hz, 1H), 7.80 (d, J=16.0 Hz, 1H), 7.72 (d, J=8.0 Hz, 2H), 7.64 (s, 1H), 7.56 (d, J=8.6 Hz, 2H), 7.37 (d, J=8.0 Hz, 2H), 7.31 (d, J=9.1 Hz, 1H), 7.22 (s, 1H), 7.09 (s, 1H), 4.08 (d, J=7.8 Hz, 3H), 3.78 (s, 2H), 2.46 (s, 3H).

(E)-N-(3-azido-5-(azidomethyl)phenyl)-2-(4-(3-(1-methyl-1H-imidazol-2-yl)-3-oxoprop-1-en-1-yl)phenyl)acetamide 40

A mixture of (E)-2-(4-(3-(1-methyl-1H-imidazol-2-yl)-3-oxoprop-1-en-1-yl)phenyl)acetic acid 46 (0.11 mmol), anhydrous DCM (4 mL), EDC (38 mg, 0.2 mmol, 1.8 equivalent) and a catalytic amount of DMAP (10 mol %) was stirred for 5 min. Then diazido-aniline (22 mg, 0.12 mmol, 1.1 equivalent) was added and the reaction mixture was stirred at room temperature overnight. The solvent was removed under reduced pressure and the residue was partitioned between ethyl acetate and brine. The combined organic extract were dried over sodium sulfate, filtrated and concentrated under reduced pressure. The crude reaction product was separated by flash chromatography on silica gel in ethyl acetate: hexanes (20%→50% ethyl acetate) to obtain 40 (32 mg, 66%). $^1$H NMR (600 MHz, CDCl$_3$) δ 8.04 (d, J=16.0 Hz, 1H), 7.77 (d, J=16.0 Hz, 1H), 7.66 (d, J=8.0 Hz, 2H), 7.40 (s, 1H), 7.32 (t, J=10.1 Hz, 2H), 7.27-7.22 (m, 2H), 7.21 (s, 1H), 7.09 (d, J=13.7 Hz, 2H), 6.68 (s, 1H), 4.25 (s, 2H), 4.08 (s, 3H), 3.72 (d, J=9.1 Hz, 2H). HRMS calculated 442.1740 found 442.1740 [M+H]$^+$ ion.

(E)-N-(4-ethynylphenyl)-2-(4-(3-(1-methyl-1H-imidazol-2-yl)-3-oxoprop-1-en-1-yl)phenyl)acetamide 41

A mixture of N-(4-ethynylphenyl)-2-(4-formylphenyl)acetamide (184 mg, 0.7 mmol), N-methyl imidazole ketone 2b (99 mg, 0.8 mmol, 1.2 equivalents), piperidine (0.2 ml, 2.1 mmol, 3 equivalents) and anhydrous methanol (5 ml) placed in a 10 mL microwave vial was heated in a microwave synthesizer at 85° C. for 6 hours. The crude reaction mixture was concentrated and purified by flash chromatography on silica gel in ethyl acetate/hexanes (20%→70% ethyl acetate) to obtain 41 (59 mg, 23%). $^1$H NMR (600 MHz, CDCl$_3$) δ 8.09 (d, J=15.9 Hz, 1H), 7.80 (d, J=16.0 Hz, 1H), 7.70 (t, J=6.9 Hz, 2H), 7.39 (s, 4H), 7.35 (d, J=8.0 Hz, 2H), 7.22 (s, 1H), 7.11 (s, 1H), 7.08 (s, 1H), 4.09 (s, 3H), 3.74 (s, 2H), 3.01 (s, 1H). HRMS calculated 370.1556 found 370.1563 [M+H]$^+$ ion.

Methyl 2-(4-(hydroxymethyl)phenyl)acetate 43

To a stirred solution of 2-(4-(hydroxymethyl)phenyl)acetic acid 42 (166.2 mg, 1 mmol) was added DBU (0.154 ml, 1 mmol, 1 equivalent), followed by the addition of Iodomethane (0.190 ml, 3 mmol, 3 equivalent). The resulting mixture was stirred overnight at room temperature and then sodium bicarbonate was added and extracted with ethyl acetate. The ethyl acetate extract was washed with 1N HCl and Brine. The organic layers were combined and dried over sodium sulfate, filtrated and concentrated under high vacuum to yield the ester 43 (178 mg, 99% yield) of $^1$H NMR (400 MHz, CDCl$_3$) δ 7.28 (dd, J=16.2, 7.1 Hz, 2H), 7.22-7.12 (m, 2H), 4.57 (s, 2H), 3.63 (s, 3H), 3.56 (d, J=9.3 Hz, 2H). $^{13}$C NMR (151 MHz, CDCl$_3$) δ 172.47 (s), 140.13 (s), 133.28 (s), 130.67-128.86 (m), 127.43 (s), 64.82 (d, J=4.7 Hz), 52.33 (s), 41.02 (s).

Methyl 2-(4-formylphenyl)acetate 44

To a stirred solution of methyl 2-(4-(hydroxymethyl) phenyl)acetate 43 in 4 ml DCM at 0° C. was added Dess Martin Periodinate (636 mg, 1.5 mmol, 1.5 equivalent). Then the reaction mixture was brought to room temperature and a mixture of 2 ml DCM and 0.02 ml of water were added slowly over 2 hours. The reaction mixture was stirred for an additional 1 hour followed by the addition of sodium bicarbonate. The resulting mixture was extracted 3 times with ethyl acetate and washed with brine. The combined organic layer was dried over sodium sulfate, filtrated and concentrated under vacuum. The crude mixture was purified by flash chromatography using ethyl acetate/hexanes (0%→50% ethyl acetate) to yield product 44. $^1$H NMR (600 MHz, CDCl$_3$) δ 9.94 (s, 1H), 7.79 (d, J=8.1 Hz, 2H), 7.40 (d, J=8.1 Hz, 2H), 3.66 (s, 2H), 3.65 (s, 3H).

Methyl (E)-2-(4-(3-(1-methyl-M-imidazol-2-yl)-3-oxoprop-1-en-1-yl)phenyl)acetate 45

Into a 10 ml microwave vial were add Methyl 2-(4-formylphenyl)acetate 44 (129 mg, 0.72 mmol), N-methyl imidazole ketone 124 mg, 1 mmol, 1.4 equivalents), piperidine (0.395 ml, 4 mmol, 5.5 equivalents) and 5 ml of anhydrous methanol. The vial was sealed and heated in the microwave synthesizer at 85° C. for 6 hours. The crude reaction mixture was concentrated and purified by flash chromatography on silica gel in ethyl acetate/hexanes (20%→70% ethyl acetate), followed by recrystallization yielding the pure product 55 62 mg, 30% yield). $^1$H NMR (600 MHz, CDCl$_3$) δ 8.03 (d, J=16.0 Hz, 1H), 7.77 (d, J=16.0 Hz, 1H), 7.62 (d, J=8.1 Hz, 2H), 7.28 (d, J=8.1 Hz, 2H), 7.18 (s, 1H), 7.05 (s, 1H), 4.05 (s, 3H), 3.67 (s, 3H), 3.62 (s, 2H).

(E)-2-(4-(3-(1-methyl-1H-imidazol-2-yl)-3-oxoprop-1-en-1-yl)phenyl)acetic acid 46

To a stirred solution of methyl (E)-2-(4-(3-(1-methyl-1H-imidazol-2-yl)-3-oxoprop-1-en-1-yl)phenyl)acetate 45 in 2.5 ml MeOH:H$_2$O (1.5:1) was added K$_2$CO$_3$ (58 mg, 0.42 mmol, 3 equivalents) and the reaction mixture was stirred overnight at room temperature. Methanol was removed on the rotary evaporator and 1 ml of sodium bicarbonate was added and the mixture was extracted with ethyl acetate. The aqueous layer was collected and acidified using concentrated HCl to pH 5, when the acid precipitated as a yellowish solid. The solid was filtrated, washed with cold water and then dissolved in a 50:50 mixture of methanol and ethyl acetate. The solution was dried over sodium sulfate filtrated, condensed under vacuum to yield pure product 46 (46 mg, 98% yield). $^1$H NMR (600 MHz, CD$_3$OD) δ 7.95 (d, J=15.9 Hz, 1H), 7.77 (d, J=15.9 Hz, 1H), 7.67 (d, J=8.1 Hz, 2H), 7.37 (d, J=9.2 Hz, 2H), 7.35 (s, 1H), 7.19 (s, 1H), 4.06 (d, J=2.9 Hz, 3H), 3.64 (s, 2H), (46 mg, 98% yield)

Compound 46 was subjected to amidation with different amines to obtain the final analogues.

Biological Screening

National Cancer Institute 60 Human Tumor Cell Line Drug Screen

The compounds synthesized were tested at the National Cancer Institute (NCI) for anti-proliferative activity in the 60 human tumor cell line assay. The results are summarized in Tables 1 and 2 below. The compounds inhibited the growth of most of the cancer cell lines to different extents. Some of the compounds exhibited higher cell growth inhibition than the FDA-approved drug vorinostat (SAHA).

TABLE 1

Mean percentage growth inhibiton activity of synthesized compounds

| Compound | Mean Growth Inhibition Activity % |
|---|---|
| 17 | 76.31 |
| 18 | 52.06 |
| 19 | 66.84 |
| 20 | 41.34 |
| 21 | 45.33 |
| 22 | 27.48 |
| 23 | 70.02 |
| 24 | 23.48 |
| 25 | 21.10 |
| 27 | 15.90 |
| 28 | 33.11 |
| 29 | 57.67 |
| 30 | 19.33 |
| 31 | 29.20 |
| 32 | 92.81 |

TABLE 2

GI$_{50}$ (μM) for representative analogues on the NCI 60 tumor cell lines.

| Cancer Panel | Cell Line | 20 | 22 | 24 | 25 | 27 | 28 | 30 | 31 |
|---|---|---|---|---|---|---|---|---|---|
| Leukemia | CCRF-CEM | 4.67 | 1.68 | 1.55 | 1.08 | 2.37 | 2.00 | 1.46 | 4.34 |
| | HL-60(TB) | 5.88 | 1.66 | 2.03 | 3.8 | 1.57 | 1.60 | 4.81 | 3.18 |
| | K-562 | ND* | 1.30 | 1.24 | ND | 1.07 | 0.82 | ND | 2.06 |
| | MOLT-4 | 5.33 | 5.74 | 2.29 | 1.8 | 4.30 | 2.32 | 1.74 | 5.28 |

TABLE 2-continued

GI$_{50}$ (μM) for representative analogues on the NCI 60 tumor cell lines.

| Cancer Panel | Cell Line | 20 | 22 | 24 | 25 | 27 | 28 | 30 | 31 |
|---|---|---|---|---|---|---|---|---|---|
| | RPMI-8226 | 1.79 | 1.27 | 0.78 | 0.857 | 1.45 | 1.02 | 0.959 | 2.28 |
| | SR | 0.99 | 1.11 | 0.843 | 0.798 | 1.16 | 0.51 | 0.796 | 0.53 |
| Non-Small Cell Lung | A549/ATCC | 9.14 | 6.94 | 6.37 | 6.9 | 6.60 | 6.43 | 1.15 | 4.16 |
| | EKVX | 1.35 | 7.46 | 5.57 | 5.68 | 6.28 | 5.50 | 1.56 | 3.59 |
| | HOP-62 | 5.24 | 2.64 | 4.8 | 3.19 | 3.75 | 4.68 | 2.16 | 3.92 |
| | HOP-92 | 1.85 | 9.11 | 4.89 | 5.74 | 6.63 | 4.51 | 2.5 | 3.32 |
| | NCI-H226 | 9.59 | 9.85 | 6.11 | 7.5 | 8.59 | 8.57 | 7.42 | 3.61 |
| | NCI-H23 | 5.85 | 1.91 | 3.42 | 2.97 | 3.24 | 3.04 | 2.04 | 4.25 |
| | NCI-322M | 6.06 | 3.35 | 4.68 | 4 | 2.57 | 2.07 | 3.99 | 3.49 |
| | NCI-460 | 6.32 | 1.72 | 3.6 | 3.43 | 2.32 | 1.80 | 1.58 | 2.64 |
| | NCI-H522 | 4.54 | 3.38 | 4.87 | 2.6 | 3.20 | 3.34 | 4.85 | 3.92 |
| Colon | COLO 205 | 7.27 | 4.54 | 5.38 | 3.01 | 3.77 | 4.39 | 9.44 | 4.29 |
| | HCC-2998 | 6.73 | 5.43 | 3.97 | 3.73 | 4.42 | 3.78 | 3.42 | 5.10 |
| | HCT-116 | 3.28 | 1.89 | 0.694 | 0.848 | 1.68 | 0.99 | 1.31 | 1.84 |
| | HCT15 | 2.01 | 1.15 | 1.04 | 0.879 | 1.25 | 1.29 | 0.999 | 1.93 |
| | HT29 | 0.955 | 1.15 | 1.09 | 0.886 | 2.40 | 2.27 | 0.889 | 5.64 |
| | KM12 | 3.09 | 2.10 | 1.11 | 1.3 | 3.39 | 1.62 | 1.51 | 3.06 |
| | SW-620 | 5.22 | 1.43 | 1.35 | 1.43 | 2.75 | 1.97 | 1.25 | 4.29 |
| CNS | SF-268 | 5.32 | 5.10 | 3.05 | 1.65 | 3.75 | 2.89 | 1.24 | 3.81 |
| | SF-295 | 7.9 | 4.74 | 4.08 | 3.33 | 5.44 | 4.55 | 7.39 | 4.41 |
| | SF-539 | 4.76 | 0.84 | 4.52 | 3.33 | 2.43 | 3.59 | 6.4 | 2.93 |
| | SNB-19 | 6.65 | 1.58 | 2.79 | 2.32 | 1.90 | 2.74 | 1.77 | 3.58 |
| | SNB-75 | 7 | 1.11 | 3.97 | 3.63 | 25.00 | 3.74 | 1.9 | 2.81 |
| | U251 | 1.59 | 1.20 | 1.22 | 1.02 | 1.57 | 1.40 | 1.1 | 1.88 |
| Melanoma | LOX IMVI | 1.29 | 1.07 | 0.469 | 0.87 | 1.03 | 0.71 | 1.07 | 0.56 |
| | MALME-3M | 25 | 7.86 | 5.18 | 6.24 | 5.93 | 5.28 | 14.2 | 16.7 |
| | M14 | ND | 5.98 | 2.58 | ND | 4.55 | 3.23 | ND | 3.02 |
| | MDA-MB-435 | 5.68 | 4.07 | 2.87 | 4.14 | 4.30 | 4.25 | 9.15 | 4.58 |
| | SK-MEL-2 | 18.1 | 7.47 | 7.09 | 5.53 | 5.06 | 7.01 | 25 | 6.26 |
| | SK-MEL-2 | 11.5 | 6.26 | 5.32 | 4.81 | 5.69 | 4.47 | 25 | 4.92 |
| | SK-MEL-5 | 18.3 | 6.06 | 5.55 | 6.17 | 4.18 | 4.45 | 14.4 | 5.74 |
| | UACC-257 | 25 | 8.67 | 7.2 | 7.24 | 6.98 | 6.99 | 25 | 14.0 |
| | UACC-62 | 8.29 | 5.92 | 4.47 | 3.94 | 4.13 | 3.51 | 6.5 | 2.83 |
| Ovarian | IGROV1 | 6.47 | 2.66 | 3.84 | 3.59 | 2.11 | 2.93 | 5.27 | 4.63 |
| | OVCAR-3 | 1.67 | 1.70 | 1.09 | 1.14 | 1.87 | 0.96 | 1.03 | 3.92 |
| | OVCAR-4 | 10.4 | 9.14 | 5.12 | 4.11 | 4.12 | 5.68 | 2.18 | 3.31 |
| | OVCAR-5 | 6.84 | 2.60 | 4.89 | 3.3 | 4.19 | 4.36 | 9.98 | 4.97 |
| | OVCAR-8 | 7.24 | 5.08 | 7.99 | 3.65 | 6.44 | 5.71 | 3.49 | 4.86 |
| | NCI/ADR-RES | 6.73 | 7.18 | 8.96 | 5.02 | 7.54 | 4.24 | 2.22 | 5.37 |
| | SK-OV-3 | 12.8 | 9.38 | 7.66 | 9.74 | 9.30 | 9.81 | 8.79 | 6.97 |
| Renal | 786-0 | 4.28 | 1.37 | 1.4 | 1.13 | 2.67 | 1.37 | 1.6 | 4.36 |
| | A498 | 19.9 | 8.93 | 4.73 | 5.48 | 6.08 | 5.56 | 25 | 3.73 |
| | ACHN | 6.51 | 4.82 | 6.33 | 4.04 | 5.24 | 5.74 | 15 | 3.95 |
| | CAKI-1 | 9.63 | ND | 4.43 | 4.88 | ND | 3.14 | 13.5 | 5.08 |
| | RXF393 | 7.68 | 3.44 | 3.75 | 3.05 | 3.86 | 3.89 | 2.97 | 3.39 |
| | SN12C | 5.91 | 2.93 | 1.87 | 2.4 | 3.84 | 1.72 | 3.04 | 3.71 |
| | TK-10 | 7.93 | 7.89 | 6.63 | 5.41 | 7.44 | 10.50 | 12.3 | 6.01 |
| | UO-31 | 3.01 | 2.64 | 2.43 | 1.69 | 2.77 | 1.72 | 2.27 | 2.65 |
| Prostatic | PC-3 | 7.1 | 2.80 | 2.81 | 2.39 | 3.29 | 1.99 | 1.37 | 7.06 |
| | DU-145 | 4.56 | 1.19 | 2.13 | 1.7 | 1.10 | 1.24 | 1.42 | 4.45 |
| Breast | MCF7 | 1.15 | 0.99 | 0.851 | 0.742 | 1.13 | 1.04 | 0.891 | 2.52 |
| | MDA-MB-231/ATCC | 9.46 | 1.83 | 2.79 | 4.27 | 2.37 | 2.96 | 5.23 | 3.36 |
| | HS 578T | 13.6 | 2.33 | 5.88 | 18.8 | 1.42 | 1.50 | 15.7 | 5.36 |
| | BT-549 | 6.42 | 2.73 | 2.11 | 3.46 | 2.95 | 1.32 | 3.53 | 2.94 |
| | T-47D | 6.47 | 3.33 | 3.97 | 3.24 | 5.23 | 8.34 | 4.3 | 3.80 |
| | MDA-MB-468 | 3.3 | 0.97 | 1.77 | 1.68 | 1.71 | 1.72 | 1.03 | 1.99 |

ND = No Data.

Mitotic Arrest

Figure 6:
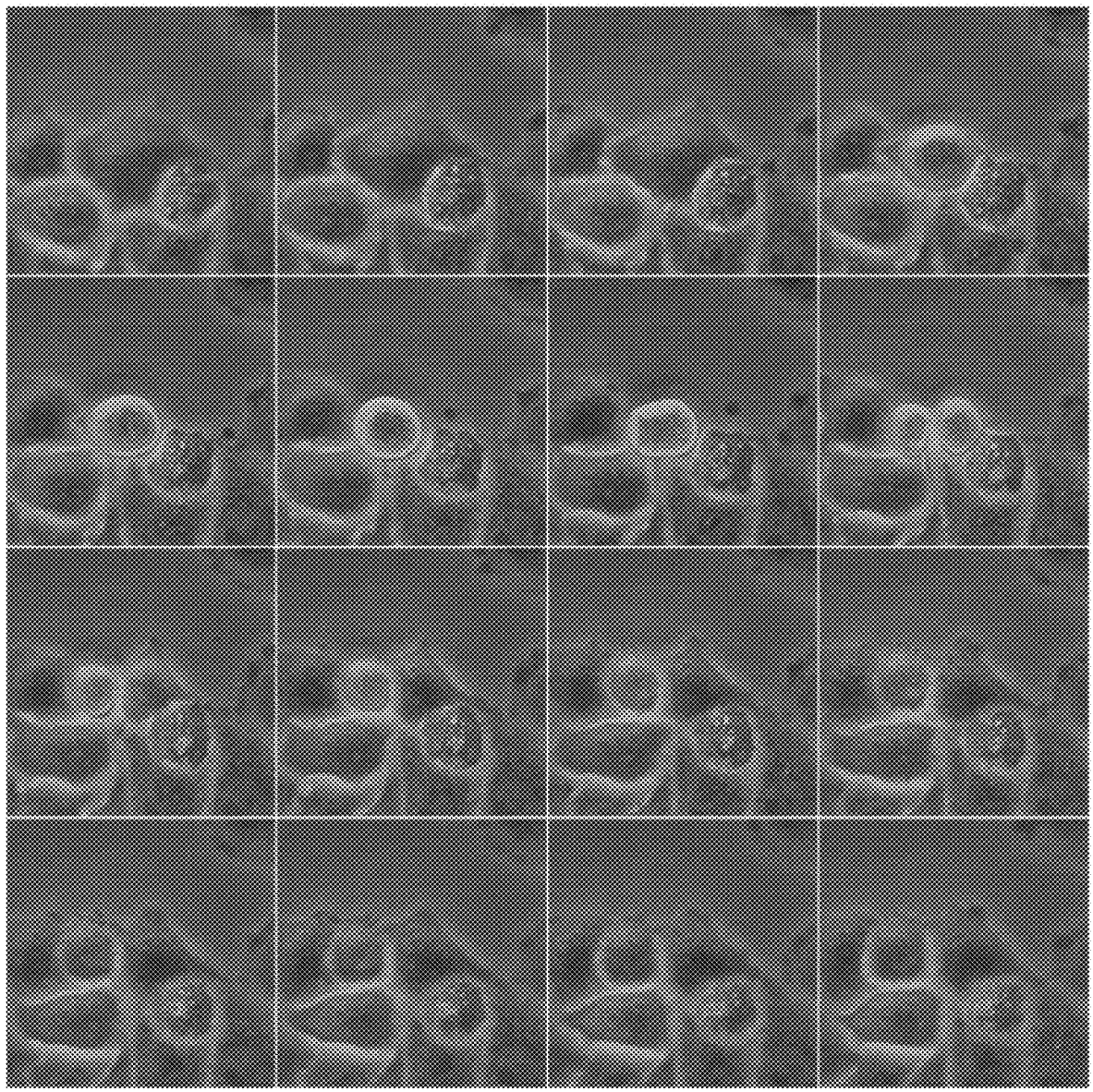
FIG. 6: Color images showing untreated HeLa cells used as a control. Mitotic duration: 60 minutes. Each frame was taken after 12 minute intervals. Frame 5 to frame 9 show cells' progression through mitosis.
Figure 7:
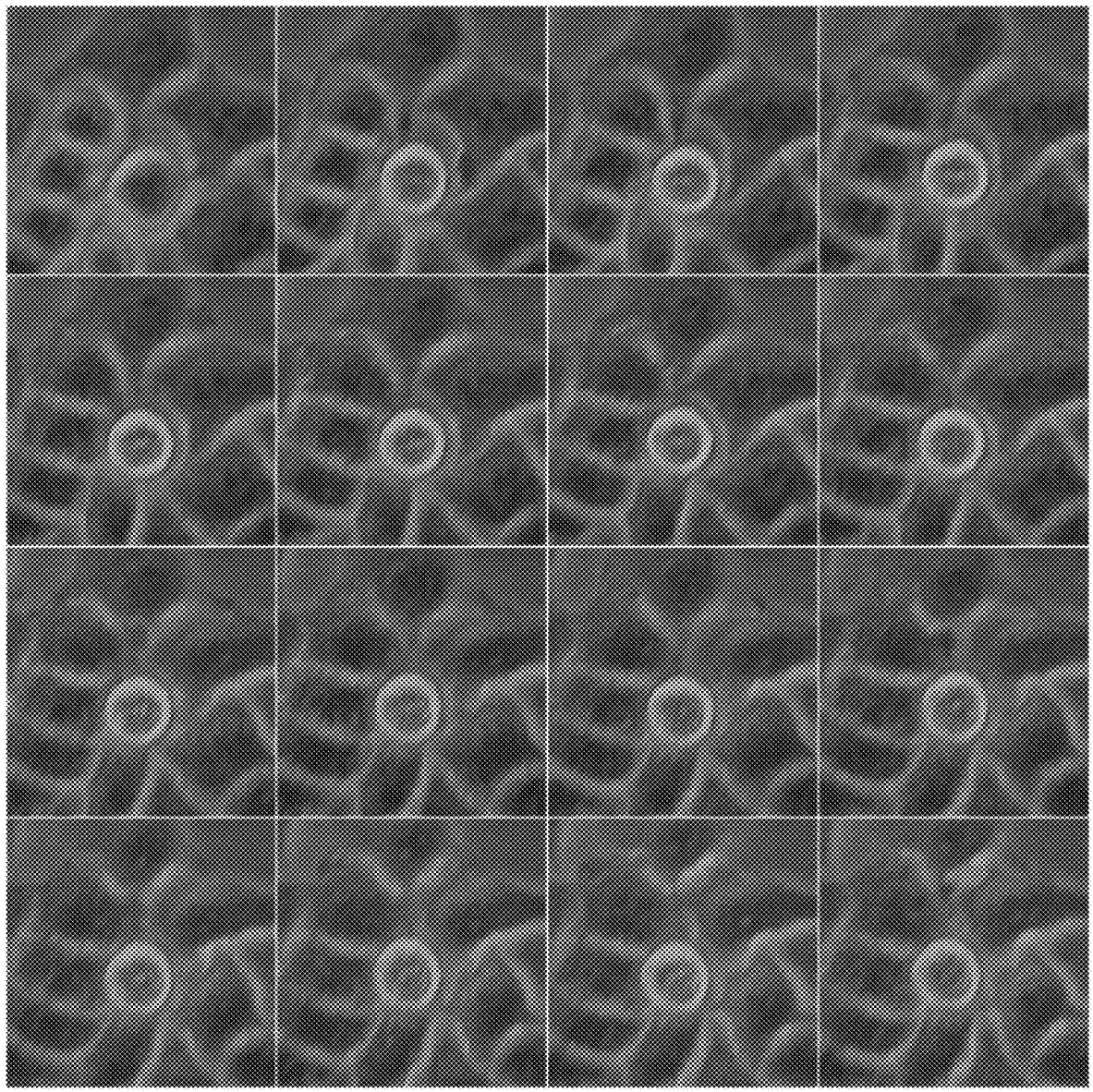
FIG. 7: Color images showing HeLa cells treated with 10 μM of compound 25. Mitotic duration: 27.4 hr.

Although developed as HDAC inhibitors, the compounds herein may actually act by multiple mechanisms. Some of the HDAC inhibitor compounds showed mitotic arrest in a cell inhibition assay. Specifically, the compounds were found to cause mitotic arrest of HeLa cells. FIG. 7 shows cells treated with compound 25 at 10 μM and observed under the microscope. Untreated cells were used as the control (FIG. 6) and observed for 60 minutes whilst the treated cells were observed for 27.4 hours. Snap shots were taken at a 12 minute interval.

A cell that is rounded up in frame 2 enters mitosis (FIG. 7). However, unlike the untreated cells which underwent normal mitotic cell division, cells treated with compound 25 did not divide at the end of an hour. The cells entered the first step of mitotic phase, became rounded, but did not proceed with cell division when monitored for over 27.4 hours. Cells eventually underwent apoptosis.

Figure 8A:
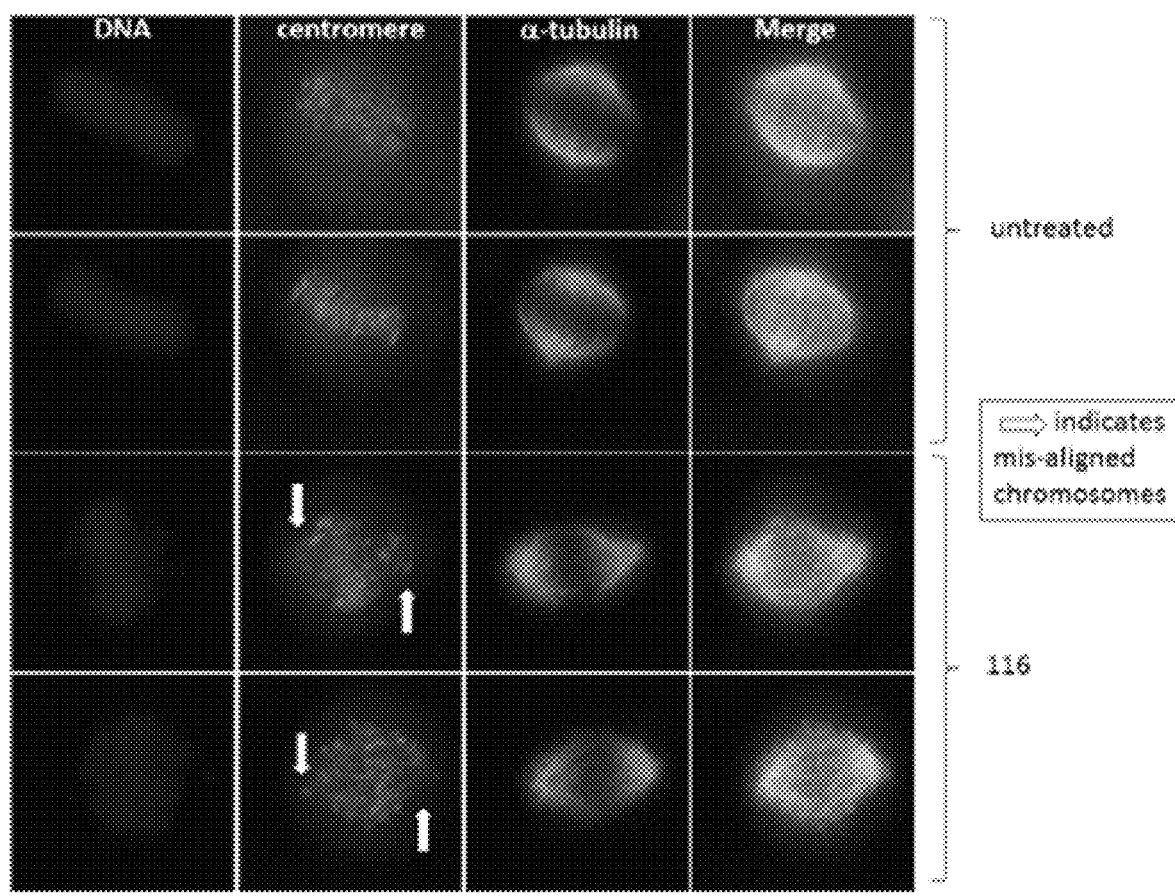
FIGS. 8A-8B: Color images showing effects of compound 25 on chromosome alignment, centromeres, and spindle body. Microtubules that make up the mitotic spindle are detected with an antibody linked to a green fluorophore, which was detected with a fluorescence microscope. Centromeres were detected with a far red fluorophore (they are pseudocolored pink). DNA was detected with Hoechst DNA stain, which is blue.
Figure 8B:
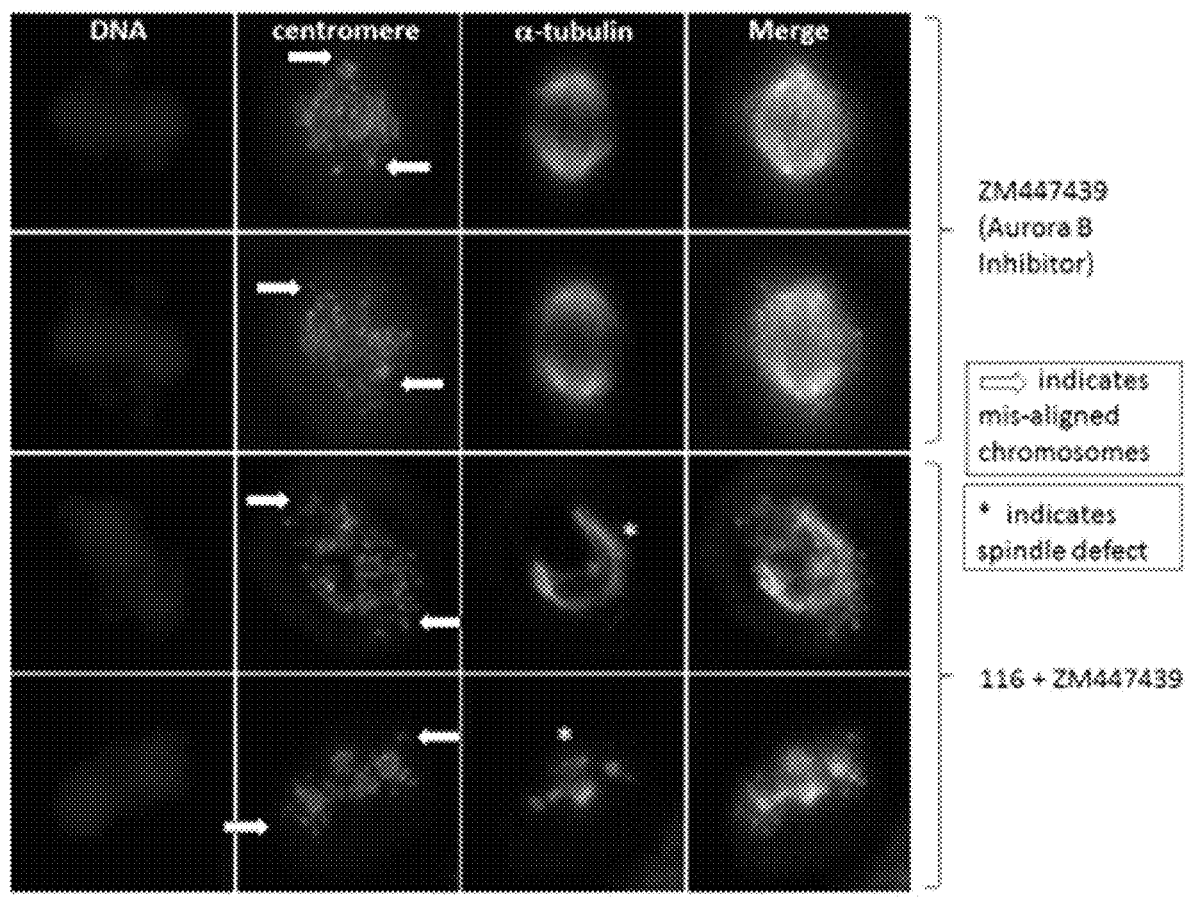

Further, in the cells treated with compound 25, the chromosomes were found to be not properly aligned on the spindle body of the cell and the centromeres were found to be scattered. However, the spindle body remained intact. In normal cells (FIG. 8A, upper two panels), chromosomes line up between the spindle poles at metaphase. In cells treated with compound 25 for several hours (FIG. 8A, lower two panels), cells still enter mitosis but centromeres are found all over the cell (not just in the middle between the poles of the spindle). The chromosomes were misaligned, indicating that the compound somehow disrupts chromosome alignment, possibly by altering attachment of centromeres to spindle microtubules. FIG. 8B shows cells treated with ZM447439 to inhibit Aurora B. Aurora B is required for proper spindle/centromere attachment and therefore, it was used the as a positive control. Many misaligned chromosomes were observed after ZM treatment. However, when ZM is combined with compound 25, what was observed was a very dramatic disruption of spindle architecture. The compound, when combined with ZM, totally obliterates proper spindle function. Without wishing to be bound by theory, it is believed that both Aurora B and the targets of compound 25 work in parallel to control tubulin function. When either one is inhibited alone, there is no effect since the other pathway compensates. When both are inhibited, the defect is detected.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound of Formula I:

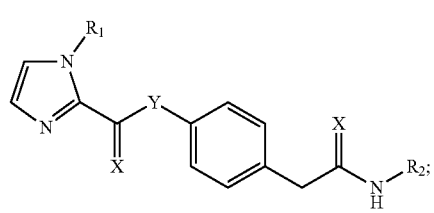

Formula I wherein:
  each X is independently O or S;
  Y is C—C, C=C, or a cyclopropyl ring;
  $R_1$ is hydrogen, alkyl, aryl, heteroaryl, aralkyl, or heteroaralkyl; and
  $R_2$ is hydrogen, alkyl, aryl, heteroaryl, aralkyl, or heteroaralkyl;
and salts, stereoisomers, racemates, hydrates, solvates, prodrugs, and polymorphs thereof.

2. The compound of claim 1, wherein each X is O and Y is C=C, such that the compound is Formula II:

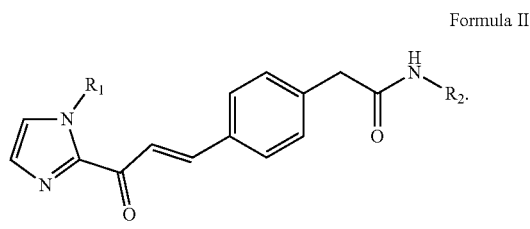

Formula II

3. The compound of claim 1, wherein each X is O and $R_1$ is H, such that the compound is Formula III:

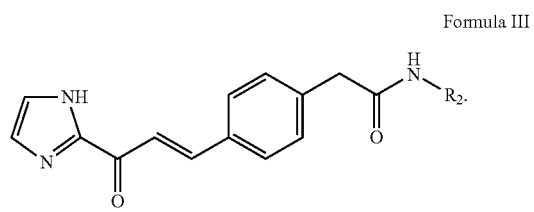

Formula III

4. The compound of claim 1, wherein each X is O and Y is a cyclopropyl ring, such that the compound is Formula IV:

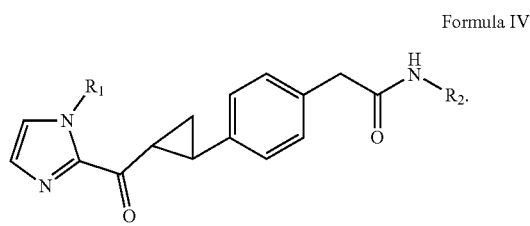

Formula IV

5. The compound of claim 1, wherein the compound is Formula V:

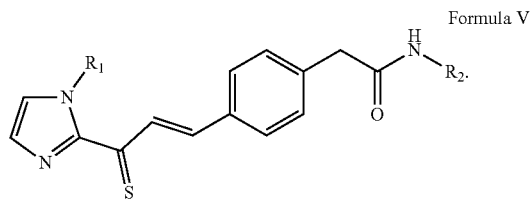

Formula V

6. The compound of claim 1, wherein the compound is Formula VI:

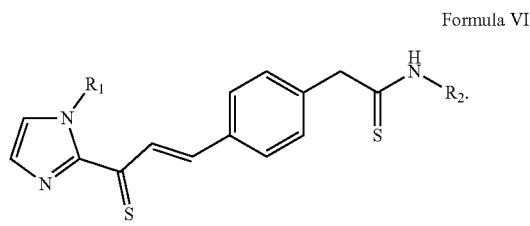

Formula VI

7. The compound of claim 1, wherein either of $R_1$ or $R_2$ is H, alkyl, substituted or unsubstituted phenyl, cyclohexyl, or napthalyl.

8. The compound of claim 1, wherein either of $R_1$ or $R_2$ is selected from the group consisting of H, methyl, ethyl, phenyl, naphthalyl, 4-dimethylaminophenyl, 4-methoxyphenyl, p-tolyl, 4-fluorophenyl, cyclohexyl, 4-trifluoromethylphenyl, and 4-chlorophenyl.

9. The compound of claim 1, wherein each of $R_1$ and $R_2$ is independently selected from the group consisting of H, methyl, ethyl, phenyl, naphthalyl, 4-dimethylaminophenyl, 4-methoxyphenyl, p-tolyl, 4-fluorophenyl, cyclohexyl, 4-trifluoromethylphenyl, and 4-chlorophenyl.

10. The compound of claim 1, wherein the compound is (E)-2-(4-(3-(1H-imidazol-2-yl)-3-oxoprop- 1-en-1-yl)phenyl)-N-(p-tolyl)acetamide 20:

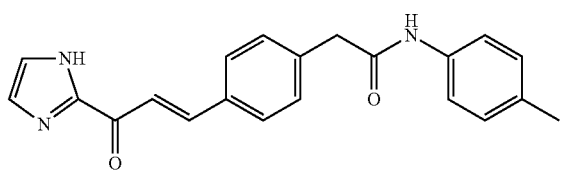

11. The compound of claim 1, wherein the compound is (E)-2-(4-(3-(1H-imidazol-2-yl)-3-oxoprop-1-en-1-yl)phenyl)-N-(4-fluorophenyl)acetamide 22:

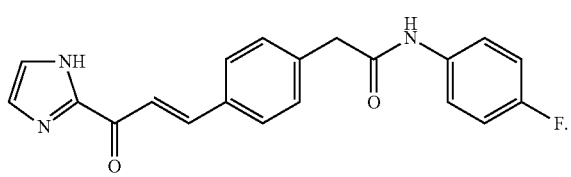

12. The compound of claim 1, wherein the compound is (E)-2-(4-(3-(1H-imidazole-2-yl)-3-oxoprop-1-en-1-yl)phenyl)-N-(4-(trifluoromethyl)phenyl)acetamide 24:

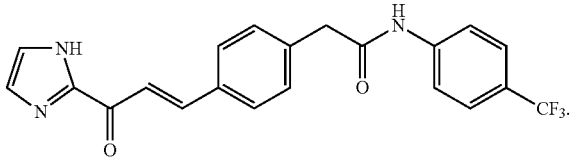

13. The compound of claim 1, wherein the compound is (E)-2-(-4(3-(1H-imidazol-2-yl)-3-oxoprop-1-en-1-yl)phenyl)-N-(4-chlorophenyl)acetamide 25:

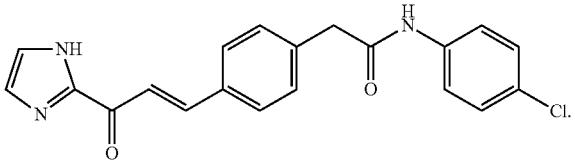

14. The compound of claim 1, wherein the compound is (E)-2-(4-(3-(1-methyl-1H-imidazol-2-yl)-3-oxoprop-1-en-1-yl)phenyl)-N-phenylacetamide 27:

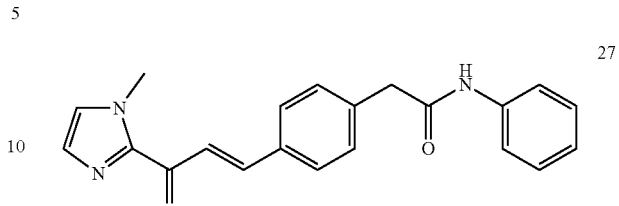

15. The compound of claim 1, wherein the compound is (E)-N-(4-fluorophenyl)-2-(4-(3-(1-methyl-1H-imidazol-2-yl)-3-oxoprop-1-en-1-yl)phenyl)acetamide 28:

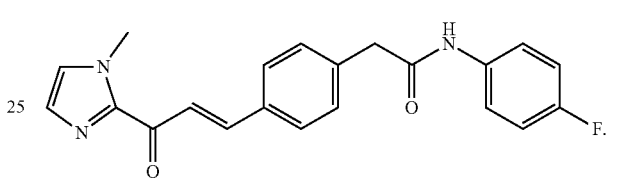

16. The compound of claim 1, wherein the compound is (E)-N-(4-chlorophenyl)-2-(4-(3-(1-methyl-1H-imidazol-2-yl)-3-oxoprop-1-en-1-yl) phenyl)acetamide 30:

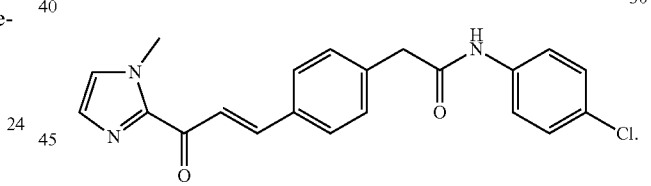

17. The compound of claim 1, wherein the compound is (E)-2-(4-(3-(1-ethyl-1H-imidazol-2-yl)-3-oxoprop-1-en-1-yl)phenyl)-N-(4-fluorophenyl)acetamide 31:

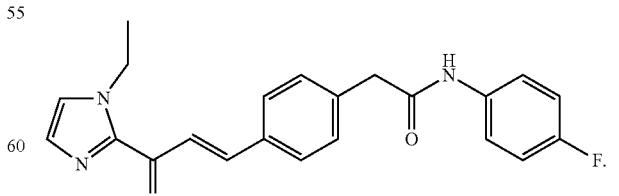

18. The compound of claim 1, wherein the compound is (E)-2-(4-(3-(1H-imidazol-2-yl)-3-oxoprop-1-en-1-yl) phenyl)-N-(3,4,5-trifluorophenyl) acetamide 33

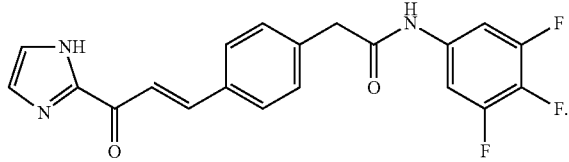

33

19. The compound of claim 1, wherein the compound is (E)-2-(4-(3-(1-methyl-1H-imidazol-2-yl)-3-oxoprop-1-en-1-yl) phenyl)-N-(3,4,5-trifluorophenyl)acetamide 34

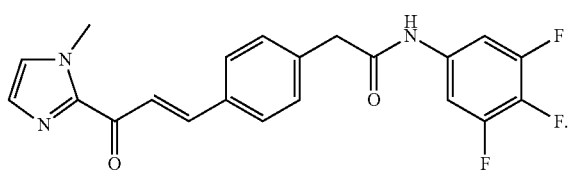

34

20. The compound of claim 1, wherein the compound is (E)-2-(4-(3-(1H-imidazol-2-yl)-3-oxoprop-1-en-1-yl) phenyl)-N-(perfluorophenyl)acetamide 35

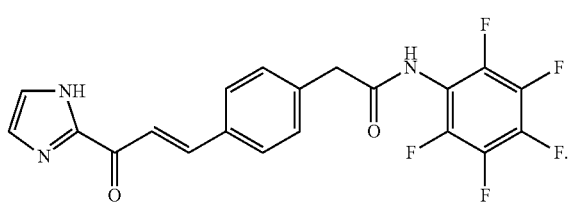

35

21. The compound of claim 1, wherein the compound is (E)-2-(4-(3-(1-methyl-1H-imidazol-2-yl)-3-oxoprop-1-en-1-yl) phenyl)-N-(perfluorophenyl)acetamide 36

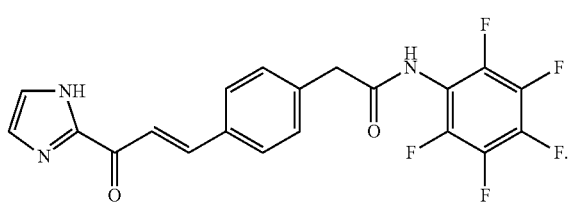

36

22. The compound of claim 1, wherein the compound is (E)-2-(4-(3-(1H-imidazol-2-yl)-3-oxoprop-1-en-1-yl) phenyl)-N-(3,5-bis(trifluoromethyl)phenyl) acetamide 37

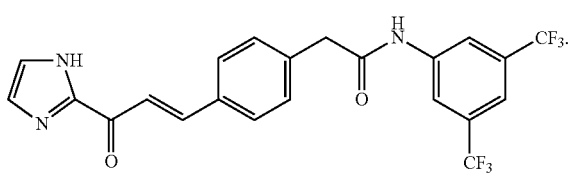

37

23. The compound of claim 1, wherein the compound is (E)-N-(3,5-Bis(trifluoromethyl)phenyl)-2-(4-(3-(1-methyl-1H-imidazol-2-yl)-3-oxoprop-1-en-1-yl) phenyl) acetamide 38

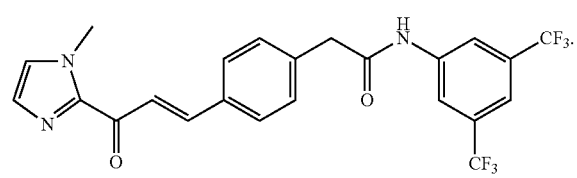

38

24. The compound of claim 1, wherein the compound is (E)-2-(4-(3-(1-methyl-1H-imidazol-2-yl)-3-oxoprop-1-en-1-yl)phenyl)-N-(4-(5-methylbenzo[d]thiazol-2-yl)phenyl) acetamide 39

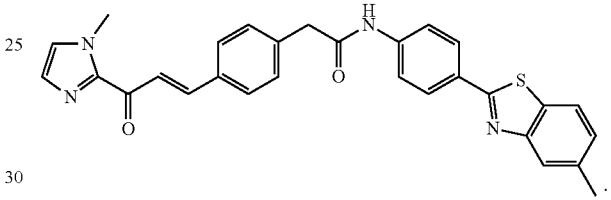

39

25. The compound of claim 1, wherein the compound is (E)-N-(3-azido-5-(azidomethyl)phenyl)-2-(4-(3-(1-methyl-1H-imidazol-2-yl)-3-oxoprop-1-en-1-yl)phenyl)acetamide 40

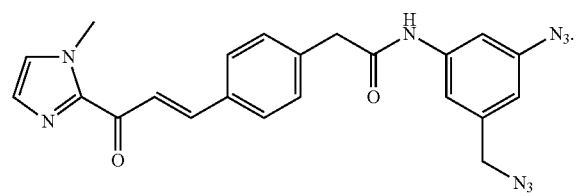

40

26. The compound of claim 1, wherein the compound is (E)-N-(4-ethynylphenyl)-2-(4-(3-(1-methyl-1H-imidazol-2-yl)-3-oxoprop-1-en-1-yl)phenyl)acetamide 41

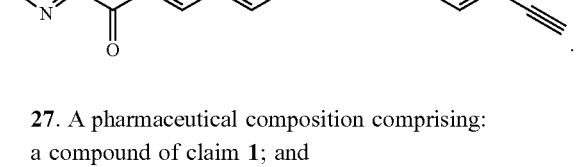

41

27. A pharmaceutical composition comprising:
a compound of claim 1; and
a pharmaceutically acceptable carrier, diluent, or adjuvant.

28. A method of making compound 39, (E)-2-(4-(3-(1-methyl-1H-imidazol-2-yl)-3-oxoprop-1-en-1-yl)phenyl)-N-(4-(5-methylbenzo[d]thiazol-2-yl)phenyl)acetamide 39

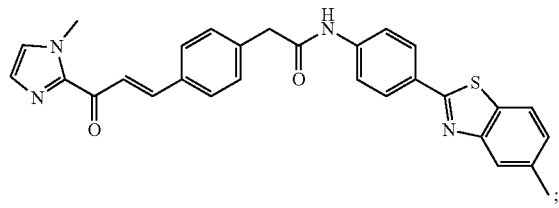

the method comprising the following steps, in order:
first, preparing Methyl 2-(4-(hydroxymethyl)phenyl)acetate 43:
- adding DBU to a stirred solution of 2-(4-(hydroxymethyl)phenyl)acetic acid 42, followed by the addition of iodomethane;
- stirring the resulting mixture overnight at room temperature and then adding sodium bicarbonate and extracting with ethyl acetate;
- washing the ethyl acetate extract with 1N HCl and brine;
- combining the organic layers and drying over sodium sulfate, filtrating and concentrating under high vacuum to yield the ester 43;

second, preparing Methyl 2-(4-formylphenyl)acetate 44:
- adding Dess Martin Periodinate to a stirred solution of methyl 2-(4-(hydroxymethyl)phenyl)acetate 43;
- bringing the reaction mixture to room temperature and a adding a mixture of DCM and water;
- stirring the reaction mixture, followed by adding sodium bicarbonate;
- extracting the resulting mixture with ethyl acetate and washing with brine;
- drying the combined organic layer over sodium sulfate, filtrating and concentrating under vacuum;
- purifying the crude mixture by flash chromatography using ethyl acetate/hexanes to yield product 44;

third, preparing Methyl (E)-2-(4-(3-(1-methyl-1H-imidazol-2-yl)-3-oxoprop-1-en-1-yl)phenyl)acetate 45:
- adding Methyl 2-(4-formylphenyl)acetate 44, N-methyl imidazole ketone, piperidine and anhydrous methanol;
- heating the crude reaction mixture, concentrating and purifying, followed by recrystallization yielding the pure product 45;

fourth, preparing (E)-2-(4-(3-(1-methyl-1H-imidazol-2-yl)-3-oxoprop-1-en-1-yl)phenyl)acetic acid 46:
- adding $K_2CO_3$ to a stirred solution of methyl (E)-2-(4-(3-(1-methyl-1H-imidazol-2-yl)-3-oxoprop-1-en-1-yl)phenyl)acetate 45, and stirring the reaction mixture at room temperature;
- removing methanol and adding sodium bicarbonate;
- extracting the mixture with ethyl acetate;
- collecting the aqueous layer and acidifying using concentrated HCl, and precipitating the acid as a yellowish solid
- filtering the solid, washing with water and dissolving in a mixture of methanol and ethyl acetate;
- drying the solution over sodium sulfate filtrated, and condensing under vacuum to yield pure product 46; and, fifth, subjecting compound 46 to amidation with an amine to obtain compound 39.

29. A method of inhibiting cancer cell proliferation, the method comprising administering to cancer cells an effective amount of a compound of claim 1, and inhibiting the proliferation of the cancer cells,
wherein the cancer is selected from the group consisting of: leukemia, non-small cell lung cancer, colon cancer, CNS cancer, melanoma, ovarian cancer, renal cancer, prostate cancer, and breast cancer.

30. A method of treating a cancer, the method comprising:
administering an effective amount of a compound of claim 1 to a subject in need thereof, and treating a cancer in the subject
wherein the cancer is leukemia, non-small cell lung cancer, colon cancer, CNS cancer, melanoma, ovarian cancer, renal cancer, prostate cancer, or breast cancer.

31. A method of disrupting chromosome alignment in a cell, the method comprising administering to a cell an effective amount of a compound of claim 1, and disrupting chromosome alignment in the cell.

32. The method of claim 31, wherein the compound is (E)-2-(-4(3-(1H-imidazol-2-yl)-3-oxoprop-1-en-1-yl)phenyl)-N-(4-chlorophenyl)acetamide 25:

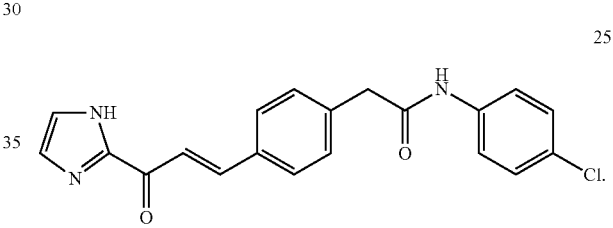

33. A method of obliterating proper spindle function in a cell, the method comprising administering to a cell an effective amount of a combination of a compound of claim 1 and an Aurora kinase inhibitor, and obliterating proper spindle function in the cell.

34. The method of claim 33, wherein the compound is (E)-2-(-4(3-(1H-imidazol-2-yl)-3-oxoprop-1-en-1-yl)phenyl)-N-(4-chlorophenyl)acetamide 25:

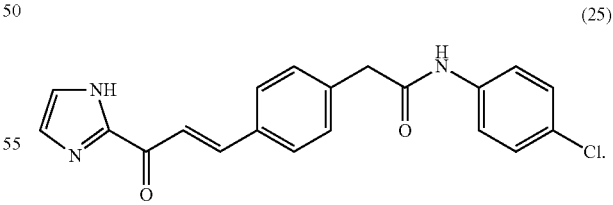

35. The method of claim 34, wherein the Aurora kinase inhibitor comprises ZM447439.

* * * * *